US008569245B2

(12) United States Patent
Luesch et al.

(10) Patent No.: US 8,569,245 B2
(45) Date of Patent: Oct. 29, 2013

(54) PROTEASE INHIBITORS, COMPOSITIONS AND METHODS OF USE

(75) Inventors: Hendrik Luesch, Gainesville, FL (US); Valerie J. Paul, Fort Pierce, FL (US); Jason C. Kwan, Salt Lake City, UT (US)

(73) Assignees: University of Florida Research Foundation, Inc., Gainesville, FL (US); Smithsonian Institution, Washington, DC (US)

( * ) Notice: Subject to any disclaimer, the term of this patent is extended or adjusted under 35 U.S.C. 154(b) by 0 days.

(21) Appl. No.: 13/380,775

(22) PCT Filed: Jun. 26, 2010

(86) PCT No.: PCT/US2010/040120
§ 371 (c)(1),
(2), (4) Date: Apr. 2, 2012

(87) PCT Pub. No.: WO2010/151852
PCT Pub. Date: Dec. 29, 2010

(65) Prior Publication Data
US 2012/0178669 A1    Jul. 12, 2012

Related U.S. Application Data

(60) Provisional application No. 61/221,027, filed on Jun. 26, 2009.

(51) Int. Cl.
*A61K 38/57* (2006.01)
(52) U.S. Cl.
USPC ........ 514/20.1; 514/21.6; 514/21.7; 530/323; 530/328
(58) Field of Classification Search
None
See application file for complete search history.

(56) References Cited

U.S. PATENT DOCUMENTS

2002/0156008 A1* 10/2002 Kaumaya et al. ............... 514/12
2006/0160746 A1*  7/2006 Gorin et al. ..................... 514/17

OTHER PUBLICATIONS

Hu, Liang et al; "Thrombin up-regulates cathepsin D which enhances angiogenesis, growth, and metastasis." Cancer Res. (2008) 68(12) p. 4666-4673.*
Tsukuba, Takayuki et al; "New functional aspects of cathepsin D and cathepsin E." Mol. Cells (2000) 10(6) p. 601-611.*
McKenzie, Brent S. et al; "Understanding the il-23-il-17 immune pathway." Trends Immunol. (2006) 27(1) p. 17-23.*
Ndhlovu, Lishomwa C. et al; "Suppression of HIV-1 plasma viral load below detection preserves IL-17 producing T cells in HIV-1 infection." AIDS (2008) 22(8) p. 990-992.*
Radtke, Andrea L. and O'Riordan, Mary X. D.; "Intracellular innate resistance to bacterial pathogens." Cell. Microbiol. (2006) 8(11) p. 1720-1729.*
Yoshida S. et al; "Anti-type V collagen lymphocytes that express IL-17 and IL-23 induce rejection pathology in fresh and well healed lung transplants." Am. J. of Transplant. (2006) 6 p. 724-735.*
Kanchan Taori et al.: Lyngbyastatins 5-7, Potent Elastase Inhibitors From Floridian Marine Cyanobacteria, *Lyngbya* spp., Journal of Natural Product. 2007, vol. 70. No. 10, pp. 1593-1600.
Susan Matthew et al; Lyngbastatiin 4, a Dolastatin 13 Analogue with Elastase and Chymotrypsin Inhibitory Activity from the Marine Cyanobacterium *Lyngbya confervoides*; Journal of Natural Product. 2007, vol. 70. No. 1, pp. 124-127.
Hendrik Luesch et al; Symplostatin 3, a New Dolastatin 10 Analogue from the Marine Cyanobacterium *Symploca* sp. VP452; Journal of Natural Product. 2002, vol. 65. No. 1, pp. 16-20.
International Preliminary Report on Patentability for PCT/US2010/040120.

* cited by examiner

*Primary Examiner* — Cecilia J Tsang
*Assistant Examiner* — Fred Reynolds
(74) *Attorney, Agent, or Firm* — Edwards Wildman Palmer LLP; Jeffrey D. Hsi; Peter F. Corless

(57) ABSTRACT

This invention relates to grassystatins A, B and C, and their isolated or purified forms. The compounds of the invention are useful as aspartic protease, gamma secretase, or metalloprotease inhibitors. Methods of using the compounds and compositions thereof are also disclosed.

7 Claims, 12 Drawing Sheets

Figure 1. NMR Spectral Data for Grassystatins A (1) and B (2) at 500 MHz ($^1$H) and 150 MHz ($^{13}$C) in CDCl$_3$

| | | | | Grassystatin A (1) | | | Grassystatin B (2) | |
|---|---|---|---|---|---|---|---|---|
| C/H no. | | $\delta_H$ (J in Hz) | $\delta_C$,[a] mult. | $^1$H–$^1$H COSY | HMBC[b] | ROESY | $\delta_H$ (J in Hz) | $\delta_C$,[a] mult. |
| O-Me-Pro | 1 | | 172.49, s | | | | | 172.4, s |
| | 2 | 4.42, dd (7.1, 7.1) | 59.2, d | 3a, 3b | 1, 3, 4 | 3a, 3b, 5a, 5b | 4.42, dd (7.7, 6.8) | 59.0, d |
| | 3a | 2.18, m | 28.9, t | 2, 3b, 4a, 4b | 1, 2, 4, 5 | 2, 3b, 4b | 2.20, m | 28.7, t |
| | 3b | 1.84, m | | 2, 3a, 4a, 4b | 1, 2, 4, 5 | 3a, 4a | 1.82, m | |
| | 4a | 1.94, m | 25.3, t | 3a, 3b, 4b, 5a, 5b | 1, 2, 3 | 3b, 4b, 5a, 5b | 1.95, m | 25.2, t |
| | 4b | 1.80, m | | 3a, 3b, 4a, 5a, 5b | 1, 2, 3, 5 | 3a, 4a, 5a, 5b | 1.81, m | |
| | 5a | 3.46, m | 47.0, t | 4a, 4b, 5b | 1, 2, 3, 4 | 2, 4a, 4b, 5b, 8 | 3.42, m | 46.8, t |
| | 5b | 3.29, m | | 4a, 4b, 5a | 3, 4, 7† | 2, 4a, 4b, 5a, 8 | 3.29, m | |
| | 6 | 3.72, s | 52.2, q | | | | 3.72, s | 52.0, q |
| N-Me-Phe | 7 | | 168.1, s | | | | | 167.9, s |
| | 8 | 5.65, dd (9.2, 6.5) | 55.7, d | 9a, 9b | 7, 9, 10, 16, 17 | 2, 5a, 5b, 9a, 9b, 16 | 5.64, dd (8.7, 6.8) | 77.8, d |
| | 9a | 3.23, dd (14.1, 6.5) | 34.7, t | 8, 9b | 7, 8, 10, 11/15 | 8, 9b, 11/15 | 3.22, dd (14.2, 6.8) | 34.5, t |
| | 9b | 2.97, dd (−14.1, 9.2) | | 8, 5a | 7, 8, 10, 11/15 | 8, 9a | 2.91, dd (−14.2, 8.7) | |
| | 10 | | 136.7, s | | | | | 136.7, s |
| | 11/15 | 7.20, m | 129.5, d | | 9, 11/15, 13 | 8, 9a, 9b, 15, 18, 19 | 7.21, m | 129.4, d |
| | 12/14 | 7.22, m | 128.2, d | | 10, 12/14 | | 7.22, m | 128.3, d |
| | 13 | 7.15, m | 126.6, d | | 11/15, | | 7.15, m | 126.5, d |
| | 16 | 3.01, s | 30.4, q | | 8, 17 | 11/15, 18, 19 | 3.04, s | 30.4, q |
| Ala/Aba | 17 | | 172.46, s | | | | | 171.7, s |
| | 18 | 4.72, dq (7.4, 7.2) | 45.5, d | 19, NH | 17, 19, 21 | 11/15, 16, 19, NH | 4.71, m | 50.3, d |
| | 19a | 0.86, d (7.2) | 17.0, q | 18 | 17, 18 | | 1.39, m | 24.5, t |
| | 19b | - | | | | | 1.29, m | |
| | 20 | - | | | | | 0.65, t (7.4) | 9.4, q |
| | NH | 7.41, d (7.4) | | 18 | 21 | 18, 22 | 7.25, m | |
| Thr | 21 | | 170.2, s | | | | | Not obs. |
| | 22 | 4.31, dd (8.0, 7.3) | 58.3, d | 23, NH | 21 | 24 | 4.35, dd (7.8, 3.1) | 58.2, d |
| | 23 | 4.19, dq (7.3, 6.3) | 67.5, d | 22, 24 | 24 | 24 | 4.19, b | 67.2,[c] d |
| | 24 | 1.12, d (6.3) | 18.9, q | 23 | 22, 23 | | 1.14, d (6.2) | 18.8, q |
| | OH | | | | | | | |
| | NH | 7.60, d (8.0) | | 22 | 25 | | 7.55, m | |
| Sta | 25 | | 172.2, s | | | | | 172.1, s |
| | 26a | 2.53, dd (−14.0, 8.7) | 40.5, t | 26b, 27 | 25, 27, 28 | | 2.54, dd (−14.0, 9.3) | 40.5, t |
| | 26b | 2.39, dd (−14.0, 5.4) | | 26a, 27 | 25, 27 | 27, 28 | 2.39, dd (−14.0, 5.4) | |
| | 27 | 4.02, dddd (8.7, 5.4, 5, 2.7) | 70.3, d | 26a, 26b, 28, OH | | 26b, 29a, 29b, 31 | 4.02, m | Not obs. |
| | 28 | 3.85 dddd (9.0, 6, 4.7, 2.7) | 51.8, d | 27, 29a, 29b, NH | | 26b, 29a, 29b, 31, 32 | 3.82, m | Not obs. |
| | 29a | 1.55, m | 39.9, t | 28, 29b, 30 | 28, 30, 31, 32 | 27, 28, 29b, 31, 32 | 1.55, m | 39.7,[c] t |
| | 29b | 1.36, ddd (−15.1, 10.2, 4.8) | | 28, 29a, 30 | 28, 30, 31, 32 | 27, 28, 29a, 31, 32 | 1.37, m | |
| | 30 | 1.61, m | 24.7, d | 29a, 29b, 31, 32 | 28, 29, 31, 32 | 29b, 31, 32 | 1.55, m | 26.7, d |
| | 31 | 0.87, m | 23.1, q | 30 | 29, 30, 32 | | 0.88, m | 22.8, q |
| | 32 | 0.84, m | 22.0, q | 30 | 29, 30, 31 | | 0.86, m | 21.9, q |
| | OH | 4.63, br | | 27 | | | | |
| | NH | 7.18, m | | 28 | | | 7.10, m | |
| Asn | 33 | | 173.2,[d] s | | | | | 172.6,[d] s |
| | 34 | 4.82, dddd (8.0, 6.2, 4.5) | 50.3, d | 35a, 35b, NH | 33, 35, 36, 37 | 35a, 35b | 4.78, m | 49.9, d |
| | 35a | 2.79, dd (−15.0, 4.5) | 37.5, t | 34, 35b | 33, 34, 36 | 34 | 2.79, dd (−15.0, 4.3) | 37.1, t |
| | 35b | 2.73, dd (−15.0, 6.2) | | 34, 35a | 33, 34, 36 | 34 | 2.68, dd (−15.0, 6.0) | |
| | 36 | | 170.6,[d] s | | | | | 170.5,[d] s |
| | NH$_a$ | 6.42, br | | | | | 6.66, br | |
| | NH$_b$ | 6.80, br | | | | | 6.23, br | |
| | NH | 7.61, d (7.5) | | 34 | | 38 | 7.53, m | |
| Leu | 37 | | 171.7, s | | | | | 168.3, s |
| | 38 | 4.35, m | 52.6, d | 39a, 39b, NH | 37, 39, 40, 43 | 39a, 39b, 41, 42 | 4.28, m | 48.8, d |
| | 39a | 1.69, m | 40.2, t | 38, 39b, 40 | 37, 38, 40, 41, 42 | 38, 41, 42, NH | 1.69, m | 39.9, t |
| | 39b | 1.62, m | | 38, 39a, 40 | 37, 38, 40, 41, 42 | 38, 41, 42, NH | 1.63, m | |
| | 40 | 1.65, m | 24.6, d | 39a, 39b, 41, 42 | 38, 39, 41, 42 | 38, 41, 42, NH | 1.64, m | 24.3, d |
| | 41 | 0.90, d (5.3) | 22.6, q | 40 | 39, 40, 42 | | 0.92, m | 22.3, q |
| | 42 | 0.85 | 22.2, q | 40 | 39, 40, 41 | | 0.88, m | 22.8, q |
| | NH | 7.05, d (5.8) | | 38 | | 39, 43 | 7.05, d (5.4) | |
| Hiva-1 | 43 | | 169.9, s | | | | | 170.1, s |
| | 44 | 5.13, d (3.3) | 78.1, d | 45 | 43, 45, 46, 47, 48 | 45, 46, 47, 51, NH (Leu) | 5.12, d (3.2) | 77.8, d |
| | 45 | 2.40, qqd (6.9, 6.9, 3.3) | 30.2, d | 44, 46, 47 | 46, 47 | 44, 46, 47 | 2.42, qqd (6.9, 6.9, 3.2) | 29.9,[c] d |
| | 46 | 0.95, d (6.9) | 19.2,[c] q | 45 | 44, 45, 47 | | 0.96, d (6.9) | 18.98, q |
| | 47 | 0.92, d (6.9) | 16.4, q | 45 | 44, 45, 46 | | 0.94, d (6.9) | 16.2, q |
| Hiva-2 | 48 | | 169.5, s | | | | | 169.4, s |
| | 49 | 4.70, d (5.9) | 77.5, d | 50 | 48, 50, 51, 52 | 44, 50, 51, 52, 54, 58/59, NH (Leu) | 4.68, d (5.9) | 77.5, d |
| | 50 | 2.20, qqd (6.8, 6.5, 5.9) | 29.8, d | 49, 51, 52 | 48, 49, 51, 52 | 49, 51, 52 | 2.20, qqd (6.8, 6.6, 5.9) | 29.5, d |
| | 51 | 1.04, d (6.5) | 17.7, q | 50 | 48, 49, 52 | | 1.06, d (6.3) | 18.5, q |
| | 52 | 1.06, d (6.8) | 18.8, q | 50 | 48, 49, 51 | | 1.05, d (6.6) | 17.6, q |
| N,N-Me$_2$-Val | 53 | | 172.46, s | | | | | 172.3, s |
| | 54 | 2.82, d (10.7) | 73.8, s | 55 | 53, 55, 56, 57, 58/59 | 49, 55, 56, 57, 58/59 | 2.83, d (10.6) | 73.6, d |
| | 55 | 1.98, m | 27.5, d | 54, 56, 57 | 53, 54, 56, 57 | 54, 56, 57, 58/59 | 1.96, m | 27.3, d |
| | 56 | 0.88, m | 19.5, q | 55 | 54, 55, 57 | | 0.99, d (6.5) | 18.90, q |
| | 57 | 0.98, d (6.5) | 19.2,[c] q | 55 | 53, 54, 55, 56 | | 0.88, m | 19.3, q |
| | 58/59 | 2.30, s | 41.1, q | | 58/59 | 49, 54 | 2.31, s | 40.9, q |

[a] Multiplicity derived from APT and HMQC spectra. [b] Protons showing long-range correlation to indicated carbon. [c] The chemical shift of these carbons was deduced by virtue of HMBC correlations, as their correlation(s) were not observed in the HMQC spectrum. [d] There is insufficient information to distinguish between carbons 33 and 36. [e] These carbons have the same chemical shift.

Figure 2. NMR Spectral Data for Grassystatin C (3) at 600 MHz in CDCl$_3$

| C/H No. | | Conformer 1[a] $\delta_H$ (J in Hz) | $\delta_C$[b] mult. | Conformer 2[a] $\delta_H$ (J in Hz) | $\delta_C$[b] mult. | $^1$H-$^1$H COSY | Key HMBC[c] | Key ROESY |
|---|---|---|---|---|---|---|---|---|
| O-Me-Pro | 1 | | 173.1, s | | 173.1, s | | | |
| | 2 | 4.35, dd (7.9, 5.4) | 58.8, d | 4.35, dd (7.9, 5.4) | 58.8, d | 3a, 3b | 1 | |
| | 3a | 2.02, m | 28.8, t | 2.02, m | 28.8, t | 2, 3b, 4a, 4b | 1 | |
| | 3b | 1.82, m | | 1.82, m | | 2, 3a, 4a, 4b | 1 | 6 |
| | 4a | 1.88, m | 24.8, t | 1.88, m | 24.8, t | 3a, 3b, 4b, 5a, 5b | | |
| | 4b | 1.72, m | | 1.72, m | | 3a, 3b, 4a, 5a, 5b | | |
| | 5a | 3.45, m | 46.7, t | 3.45, m | 46.7, t | 4a, 4b, 5b | | H-8 |
| | 5b | 3.05, m | | 3.05, m | | 4a, 4b, 5a | | |
| | 6 | 3.72, s | 52.3, q | 3.72, s | 52.3, q | | 1 | 3b |
| N-Me-Phe | 7 | | 168.6, s | | 168.6, s | | | |
| | 8 | 5.45, dd (8.8, 6.4) | 56.2, d | 5.40, dd (8.8, 6.3) | 56.4, d | 9a, 9b | 16, 17 | H-5a, 16 |
| | 9a | 3.27, m | 35.4, t | 3.27, m | 35.4, t | 8, 9b | 7 | 16 |
| | 9b | 2.83, m | | 2.83, m | | 8, 9a | 7 | 16 |
| | 10 | | 136.7, s | | 136.7, s | | | |
| | 11/15 | 7.21, m | 129.3, d | 7.21, m | 129.3, d | 12/14 | | |
| | 12/14 | 7.25, m | 128.5, d | 7.25, m | 128.5, d | 11/15, 13 | | |
| | 13 | 7.19, m | 126.8, d | 7.19, m | 126.8, d | 12/14 | | |
| | 16 | 3.057, s | 30.0, q | 3.061, s | 30.0, q | | 8, 17 | 8, 9a, 9b, 18a, 18b |
| Gly | 17 | | 168.8, s | | 168.8, s | | | |
| | 18a | 4.11, dd (-17.4, 4.7) | 41.2, t | 4.23, dd (-17.1, 5.5) | 41.1, t | 18b, NH | 17, 19 | 16 |
| | 18b | 3.94, dd (-17.4, 3.7) | | 3.82, dd (-17.1, 3.8) | | 18a, NH | 17, 19 | 16 |
| | NH | 7.49, dd (4.7, 3.7) | | 7.70, dd (5.5, 3.8) | | 18a, 18b | 19 | 20 |
| Ile | 19 | | 171.8, s | | 171.8, s | | | |
| | 20 | 4.50, dd (8.0, 5.7) | 57.9, d | 4.56, dd (9.2, 4.4) | 57.8, d | 21, NH | 19, 25 | NH (Gly) |
| | 21 | 2.01, m | 36.6, d | 2.13, m | 36.5, d | 20, 22, 23b | | |
| | 22 | 0.91, m | 15.7, q | 0.93, m | 11.8, q | 21 | | |
| | 23a | 1.48, m | 24.3, t | 1.46, m | 24.3, t | 23b, 24 | | |
| | 23b | 1.12, m | | 1.12, m | | 22, 23a, 24 | | |
| | 24 | 0.88, m | 11.7, q | 0.88, m | 11.7, q | 23a, 23b | | |
| | NH | 7.25, m | | 7.40, d (8.9) | | 20 | 25 | 26a, 26b |
| Sta | 25 | | 172.6, s | | 173.0, s | | | |
| | 26a | 2.48, dd (-13.9, 9.3) | 38.7, t | 2.56, dd (-13.3, 9.6) | 38.2, t | 26b, 27 | 25 | NH (Ile) |
| | 26b | 2.35, m | | 2.39, m | | 26a, 27 | 25 | NH (Ile) |
| | 27 | 3.92, m | 72.3, d | 3.95, m | 73.7, d | 26a, 26b, 28, OH[d] | | |
| | 28 | 3.98, m | 52.0, d | 4.07, m | 52.5, d | 27, 29, NH | 33 | |
| | 29 | 1.35, m (2H) | 38.9, t | 1.35, m (2H) | 38.9, t | 28, 30 | | |
| | 30 | 1.45, m | 24.7, d | 1.45, m | 24.7, d | 29, 31, 32 | | 38 |
| | 31 | 0.88, m | 23.7, q | 0.84, m | 23.3, q | 30 | | |
| | 32 | 0.83, m | 21.2, q | 0.83, m | 21.2, q | 30 | | |
| | OH | 4.78, b | | 4.78, b | | 27[d] | | |
| | NH | 6.49, b | | 7.92, d (8.5) | | 28 | 33 | 34 |
| N-Me-Gln | 33 | | 170.2, s | | 170.2, s | | | |
| | 34 | 5.09, m | 55.8, d | 5.07, m | 59.5, d | 35a, 35b | 33, 38, 39 | 38, 40, NH (Sta) |
| | 35a | 2.36, m | 23.7, t | 2.60, m | 25.9, t | 34, 35b, 36a, 36b | | 38 |
| | 35b | 1.85, m | | 1.64, m | | 34, 35a, 36a, 36b | 33, 37 | 38 |
| | 36a | 2.30, m | 32.5, t | 2.51, m | 33.1, t | 35a, 35b, 36b | 37 | |
| | 36b | 2.14, m | | 2.22, ddd (14.1, 8.5, 5.6) | | 35a, 35b, 36a | 37 | 38 |
| | 37 | | 175.0, s | | 175.0, s | | | |
| | 38 | 3.02, s | 30.3, q | 2.74, s | 29.1, q | | 34, 39 | 30, 32, 34, 35a, 35b, 36b, 40, 41b, 43/44 |
| | NH$_2$a | 6.45, b | | 6.43, b | | | NH$_2$b | |
| | NH$_2$b | 6.15, b | | 6.14, b | | | NH$_2$a | |
| Leu | 39 | | 173.5, s | | 172.3, s | | | |
| | 40 | 4.85, m | 47.9, d | 4.87, m | 46.9, d | 41a, 41b, NH | 39 (w), 45 (w) | 34, 38 |
| | 41a | 1.67, m | 40.8, t | 1.78, m | 41.0, t | 40, 41b, 42 | 39 | |
| | 41b | 1.32, m | | 1.53, m | | 40, 41a, 42 | 39 | 38 |
| | 42 | 1.66, m | 24.7, t | 1.66, m | 24.7, t | 41a, 41b, 43, 44 | | |
| | 43 | 0.97, m | 21.2, q | 0.94, m | 21.9, q | 42 | | 38 |
| | 44 | 0.93, m | 23.4, q | 0.97, m | 23.2, q | 42 | | 38 |
| | NH | 7.27, m | | 7.19, m | | 40 | 45 | |
| Hmpa | 45 | | 174.3, s | | 175.1, s | | | |
| | 46 | 4.11, m | 74.1, d | 4.11, m | 74.1, d | 47 | 45 | |
| | 47 | 1.83, m | 38.5, d | 1.83, m | 38.5, d | 46, 48, 49a, 49b | | |
| | 48 | 0.80, d (6.8) | 12.8, q | 0.76, d (5.8) | 12.4, q | 47 | | |
| | 49a | 1.45, m | 26.2, t | 1.45, m | 26.2, t | 47, 49b, 50 | | |
| | 49b | 1.31, m | | 1.31, m | | 47, 49a, 50 | | |
| | 50 | 0.92, m | 11.8, q | 0.92, m | 11.8, q | 49a, 49b | | |
| | OH | | | | | | | |

[a]Conformers 1 and 2 were the most prominent, and they were evident in approximately a 2.45:1 ratio. [b]Multiplicity derived from APT and HMQC spectra. [c]Protons showing long-range correlation to indicated carbon. [d]Correlation apparent for conformer 2 only.

Figure 3. IC$_{50}$s of Grassystatins A–C (1–3) against Aspartic and Metalloproteases Identified in the Primary Screen

| Protease | Grassystatin A (1) | Grassystatin B (2) | Grassystatin C (3) | Pepstatin A[a] | GM6001[a] |
|---|---|---|---|---|---|
| Cathepsin D | 26.5 ± 5.4 nM | 7.27 ± 0.90 nM | 1.62 ± 0.3 μM | 173 ± 9.9 pM | |
| Cathepsin E | 886 ± 135 pM | 354 ± 192 pM | 42.9 ± 1.7 nM | 181 ± 8.5 pM | |
| ADAM9 | 46.1 ± 21.7 μM[b] | 85.5 ± 4.0 μM[b] | >100 μM[b] | | 56.3 ± 6.4 nM |
| ADAM10 | >100 μM[b] | 87.2 ± 17.1 μM[b] | >100 μM[b] | | 263 ± 9.2 nM |
| TACE | 1.23 ± 0.21 μM[b] | 2.23 ± 0.23 μM[b] | 28.6 ± 3.2 μM[b] | | 13.1 ± 1.8 nM |

[a]IC$_{50}$s of positive controls. [b]These IC$_{50}$s were calculated from the later part of the progress curves, as time-dependent inhibition was evident.

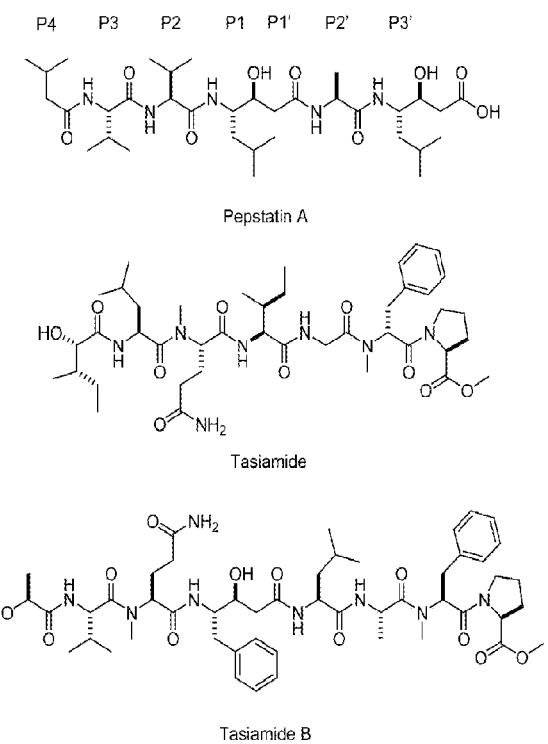
Figure 4. Structures of pepstatin A (including binding site nomenclature)), tasiamide and tasiamide B.

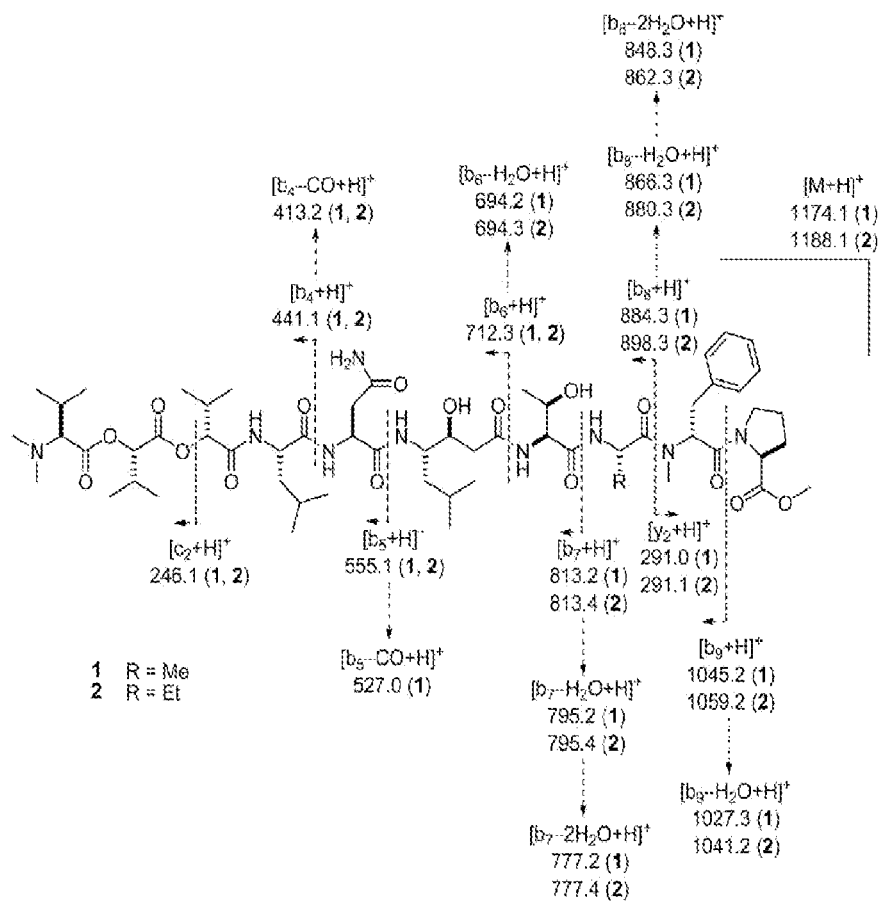
Figure 5. ESIMS fragmentation pattern of grassystatins A (1) and B (2).

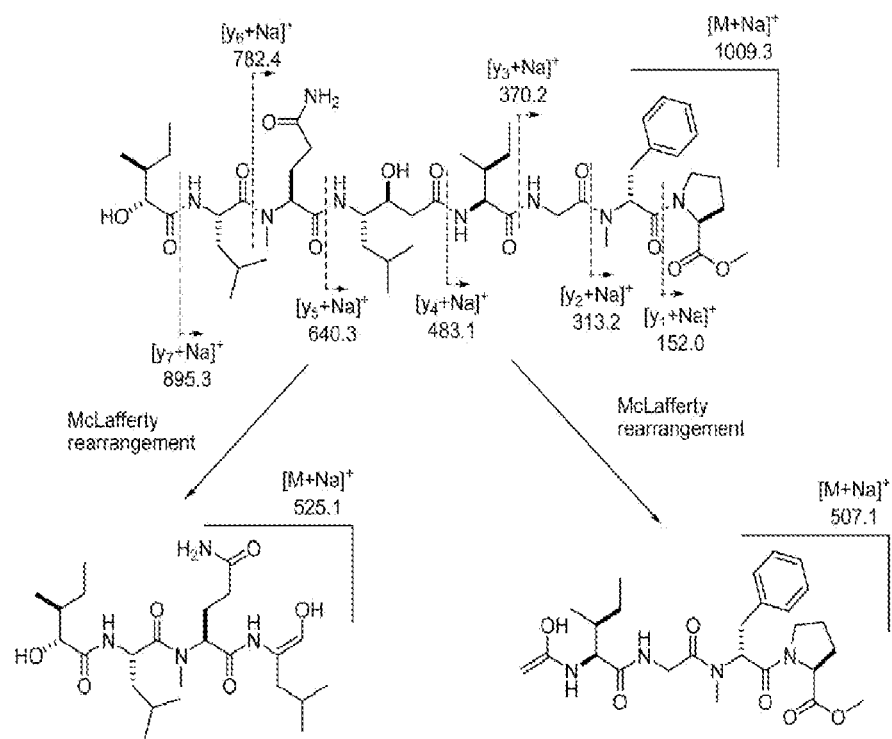
Figure 6. ESIMS fragmentation pattern for grassystatin C (3).

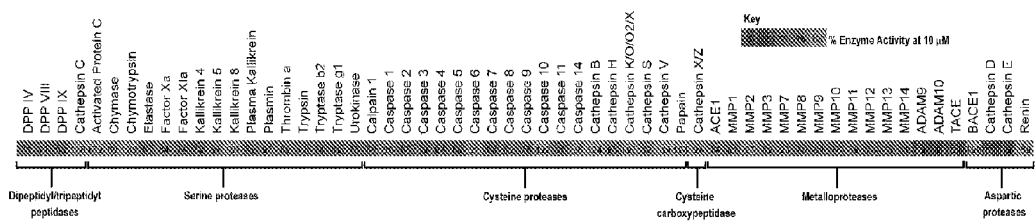
Figure 7. Protease screen treated with grassystatin A (1), 10 μM. Values represent % enzyme activity compared to solvent control, and additionally represented by a continuous color scale (0% red, 100% green).

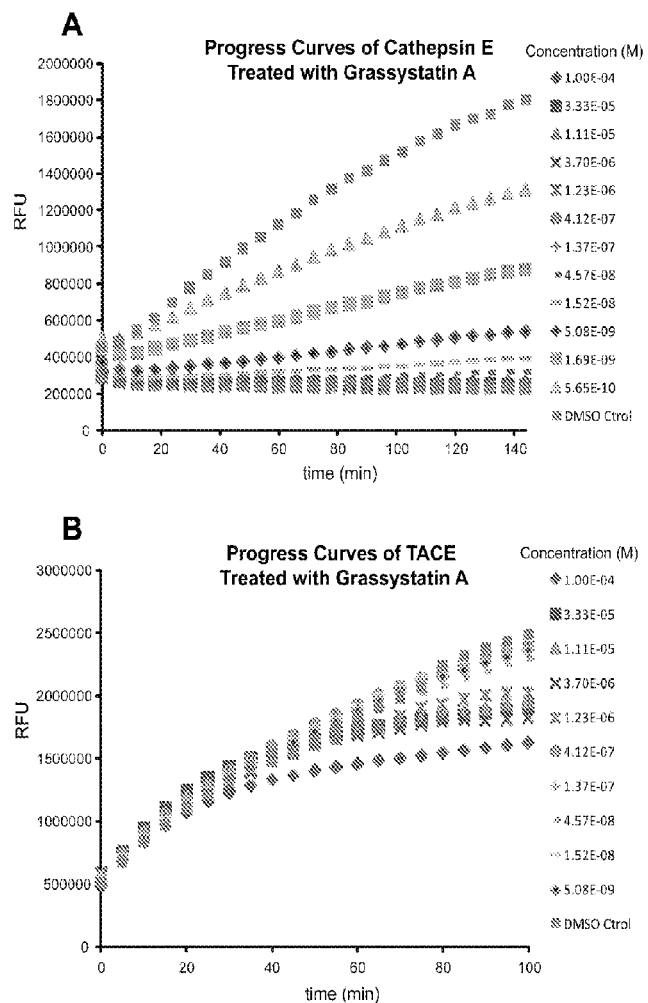
Figures 8 (A-B). Progress curves of cathepsin E and TACE treated with grassystatin A (1). A) Inhibition of cathepsin E is not time-dependent, and initial rate is affected by 1. B) Inhibition of TACE is time-dependent, and so initial rate is not affected by 1 as the onset of inhibition is slow.

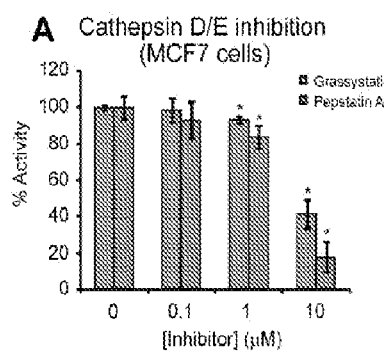 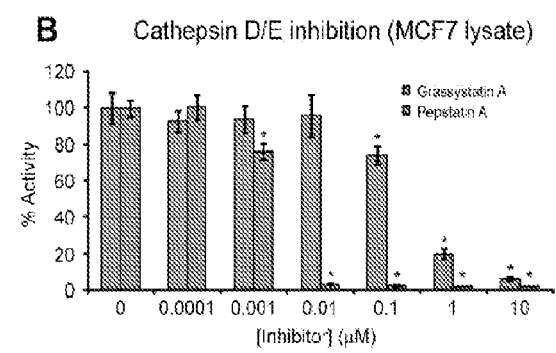
Figures 9(A-B)

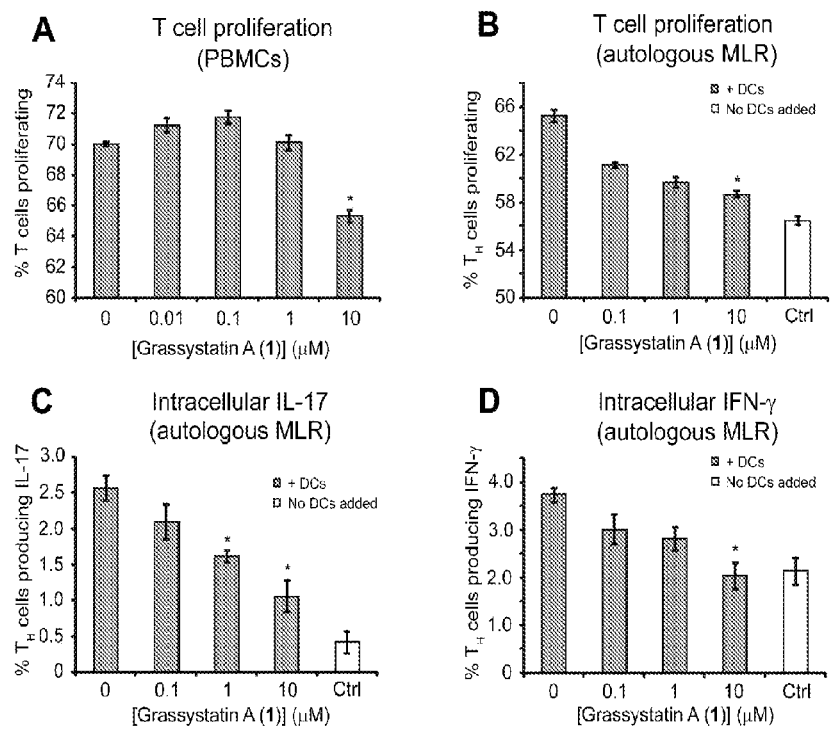
Figures 10(A-D). Downregulation of antigen presentation of T cells and $T_H$ cells after treatment with grassystatin A (1) on activated PBMC and DC

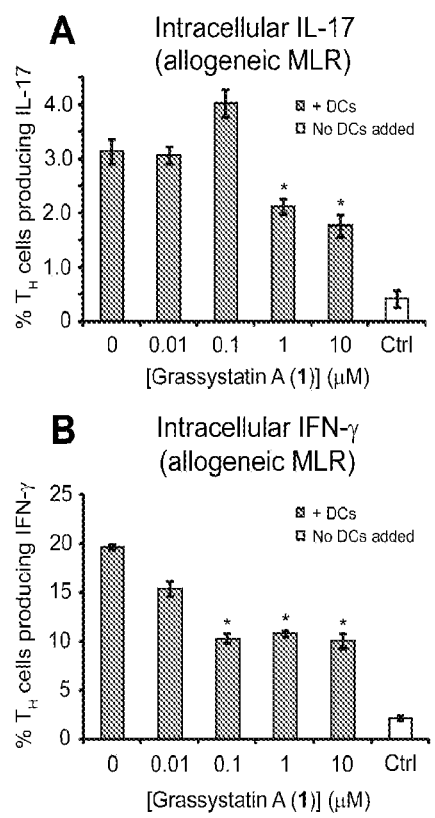
Figures 11 (A-B)

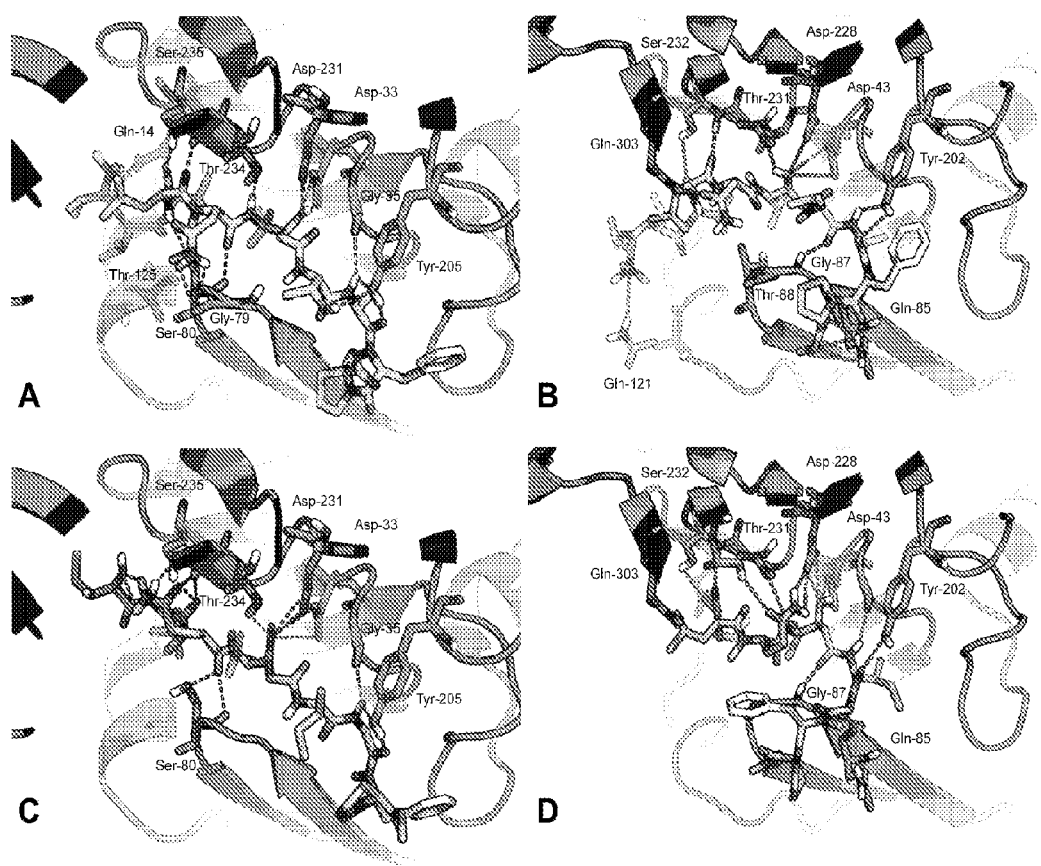
Figures 12 (A-D). Docked structures of grassystatins A (1) and C (3) with cathepsins D and E.

PROTEASE INHIBITORS, COMPOSITIONS AND METHODS OF USE

CROSS-REFERENCE TO RELATED APPLICATIONS

This application is the U.S. National Phase Application of PCT/US2010/040120, filed Jun. 26, 2010, which, claims the benefit of the following U.S. Provisional Application No. 61/221,027, which was filed on Jun. 26, 2009; the entire contents of each of these applications is hereby incorporated by reference.

STATEMENT OF RIGHTS TO INVENTIONS MADE UNDER FEDERALLY SPONSORED RESEARCH

This work was supported in part by a National Institutes of Health/NIGMS Grant, Grant No. P41GM086210. The Government has certain rights in the invention.

BACKGROUND OF THE INVENTION

Proteases are involved in diverse processes, such as blood coagulation, the cell cycle, infection and neurodegenerative disorders (Turk et al., *Nat. Rev. Drug Discov.* 2006, 5, 785-799; López-Otín et al., *J. Biol. Chem.* 2008, 283, 30433-30437). They are therefore attractive drug targets. However, non-selective inhibition of proteases can caused serious side effects. For example, non-selective inhibition of metalloproteases is thought to be the reason for musculoskeletal side effects seen in early matrix metalloprotease (MMP) inhibitors that were evaluated for cancer treatment (Coussens et al., *Science* 2002, 295, 2387-2392).

Modified peptides have potential for use as protease inhibitors. Efforts have been made to search for protease inhibitors amongst natural products produced by marine cyanobacteria (see Matthew et al., *J. Nat. Prod.* 2007, 70, 124-127; and Taori et al., *J. Nat. Prod.* 2007, 70, 1593-1600). This group of organisms is known to produce a vast array of secondary metabolites, among which there are lipophilic modified peptides that possess potent cytotoxicity (Luesch et al., *J. Am. Chem. Soc.* 2001, 123, 5418-5423; Taori et al., *J. Am. Chem. Soc.* 2008, 130, 1806-1807).

In recent years, with new developments in the areas of separation science, spectroscopic techniques, and microplate-based ultrasensitive in vitro assays, there has been a remarkable resurgence of interest in natural product research, for example, to find novel natural products that can be used as selective protease inhibitors.

SUMMARY OF THE INVENTION

In one aspect, the invention provides an isolated and/or purified compound selected from the group consisting of grassystatins A (1), B (2), and C (3) with the following structures:

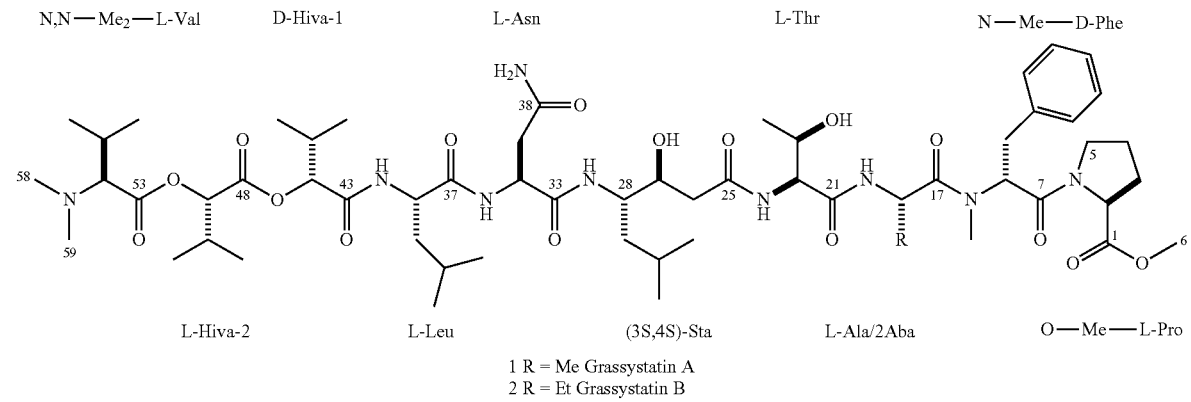

1 R = Me Grassystatin A
2 R = Et Grassystatin B

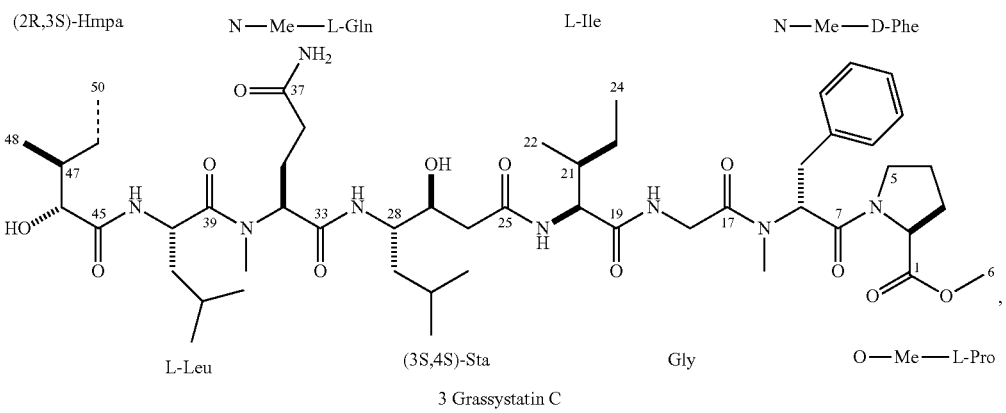

3 Grassystatin C or a pharmaceutically acceptable salt, ester, amide, hydrate, stereoisomer, or solvate thereof.

In another aspect, the invention provides a pharmaceutical composition comprising a compound selected from the group of grassystatins A, B and C, or a pharmaceutically acceptable salt, ester, amide, hydrate, stereoisomer, or solvate thereof, together with a pharmaceutically acceptable carrier or diluent.

In another aspect, the invention provides a method of treating an aspartic protease related disease or disorder in a subject (e.g., a subject identified as in need of such treatment), wherein the method comprises administering to the subject an effective amount of a compound selected from the group of grassystatins A, B and C, or a pharmaceutically acceptable salt, ester, amide, hydrate, stereoisomer, or solvate thereof. In certain embodiments, the aspartic protease related disease or disorder is a disorder related to cathepsin D or cathepsin E.

The invention also provides a method of treating a metalloprotease related disease or disorder in a subject (e.g., a subject identified as in need of such treatment), wherein the method comprises administering to the subject an effective amount of a compound selected from the group of grassystatins A, B and C, or pharmaceutically acceptable salt, ester, amide, hydrate, stereoisomer, or solvate thereof. In certain embodiments, the metalloprotease related disease or disorder is a TACE (tumor necrosis factor (TNF)-converting enzyme) related disease or disorder.

In another aspect, the invention provides a method of inhibiting a metalloprotease in vitro, in a subject, or in a cell.

In another aspect, the invention provides a method of treating a disease or disorder in a subject (e.g., a subject identified as being in need of such treatment), wherein the method comprises administering to the subject an effective amount of a compound selected from the group of grassystatins A, B and C, or a pharmaceutically acceptable salt, ester, amide, hydrate, stereoisomer, or solvate thereof. In certain embodiments, the disease or disorder is selected from the group consisting of disorders of blood coagulation, disorders of the cell cycle, infection, neurodegenerative disorders, autoimmune disorders, allergic diseases, cancer, human immunodeficiency virus (HIV) infection, AIDS, transplant rejection, and intracellular pathogen related diseases. In certain embodiments, the disease or disorder is rheumatoid arthritis or asthma.

The invention also provides a method of inhibiting T-cell proliferation in a subject (e.g., a subject identified as being in need of such treatment), in which the subject is administered an effective amount of a compound selected from the group of grassystatins A, B and C, or a pharmaceutically acceptable salt, ester, amide, hydrate, stereoisomer, or solvate thereof.

In another aspect, the invention provides a method of reducing IL-17 production in a subject (e.g., a subject identified as being in need of such treatment) or in a cell, wherein the method comprises administering to the subject or the cell an effective amount of a compound selected from the group of grassystatins A, B and C, or a pharmaceutically acceptable salt, ester, amide, hydrate, stereoisomer, or solvate thereof.

Another aspect of the invention provides a method of reducing IFN-γ production in a subject (e.g., a subject identified as being in need of such treatment) or in a cell, wherein the method comprises administering to the subject or the cell an effective amount of a compound selected from the group of grassystatins A, B and C, or a pharmaceutically acceptable salt, ester, hydrate, stereoisomer, or solvate thereof.

The invention further provides a method of inhibiting cathepsin E and/or cathepsin D in vitro, in a subject, or in a cell, wherein the method comprises contacting cathepsin E and/or cathepsin D with a compound selected from the group of grassystatins A, B and C, or a pharmaceutically acceptable salt, ester, amide, hydrate, stereoisomer, or solvate thereof.

In another aspect, the invention provides a method of inhibiting gamma secretase in vitro, in a subject (e.g., a subject identified as being in need of such treatment), or in a cell, by contacting gamma secretase with a compound selected from the group of grassystatins A, B and C, or a pharmaceutically acceptable salt, ester, amide, hydrate, stereoisomer, or solvate thereof.

In another aspect, the invention relates to a method of treating a gamma secretase-related disease or disorder in a subject (e.g., a subject identified as being in need of such treatment). The method comprises the step of administering to the subject an effective amount of a compound selected from the group of grassystatins A, B and C, or a pharmaceutically acceptable salt, ester, amide, hydrate, stereoisomer, or solvate thereof. In certain embodiments, the gamma secretase-related disease or disorder is Alzheimer's disease.

In other aspects, the invention provides methods for treatment of conditions associated with excess production of IFN-γ, or IL-17, or excess proliferation of T-cells.

The invention also provides methods for isolation, structure determination, and biological determination of grassystatins A, B and C, or a pharmaceutically acceptable salt, ester, amide, hydrate, stereoisomer, or solvate thereof.

The invention also provides methods of designing, evaluating and identifying a compound which is capable of selectively inhibiting proteases, including aspartic and metalloproteases.

The invention also provides the use of a compound selected from the group consisting of grassystatins A, B and C, or a pharmaceutically acceptable salt, ester, amide, hydrate, stereoisomer, or solvate thereof, for the manufacture of a medicament for treatment of a disease or condition identified herein.

Other embodiments of the invention are disclosed infra.

BRIEF DESCRIPTION OF THE DRAWINGS

The present invention is further described below with reference to the following non-limiting examples and with reference to the following figures, in which:

FIG. 1 is a table presenting NMR spectral data for grassystatins A (1) and B (2) at 500 MHz ($^1$H) and 150 MHz ($^{13}$C) in CDCl$_3$;

FIG. 2 is a table presenting NMR spectral data for grassystatin C (3) at 600 MHz in CDCl$_3$;

FIG. 3 is a table presenting IC$_{50}$ values of grassystatins A-C (1-3) against aspartic and metalloproteases identified in the primary screen;

FIG. 4 shows structures of pepstatin A (including binding site nomenclature), tasiamide and tasiamide B;

FIG. 5 is a figure demonstrating ESIMS fragmentation patterns of grassystatins A (1) and B (2);

FIG. 6 demonstrates ESIMS fragmentation pattern for grassystatin C (3);

FIG. 7 is a graphical representation of a protease screen showing enzyme activities when treated with grassystatin A (1), 10 μM (with values representing % enzyme activity compared to solvent control, and additionally represented by a continuous scale);

FIGS. 8 (A-B) show progress curves of cathepsin E and TACE treated with grassystatin A (1): FIG. 8A shows that inhibition of cathepsin E is not time-dependent, and initial rate is affected by grassystatin A (1); and FIG. 8B shows that inhibition of TACE is time-dependent, and that initial rate is not affected by grassystatin A (1);

FIGS. 9 (A-B) show activities of grassystatin A (1) and pepstatin A against MCF7 cellular proteases as determined with cathepsin D/E substrate: FIG. 9A shows protease activities of lysates of MCF7 cells (lysed) that were treated with grassystatin A (1) or pepstatin A; FIG. 9B relate to MCF7 cell lysate directly treated with grassystatin A (1) or pepstatin A;

FIGS. 10 (A-D) demonstrate downregulation of antigen presentation of T cells and $T_H$ cells after treatment with grassystatin A (1) on activated PBMC and DC: FIG. 10A shows that downregulation of the activation of $CD3^+$ T cells on whole PBMC after treatment with different concentrations of grassystatin A (1); FIG. 10B shows downregulation of $T_H$ activation (proliferation) by the addition of different concentrations of grassystatin A (1); FIGS. 10C and 10D show effect of grassystatin A (1) on the production of intracellular IFN-γ (FIG. 10C) and IL-17 (FIG. 10D) by $T_H$ cells induced by autologous activated DC;

FIGS. 11 (A-B) show effect of grassystatin A (1) on the production of intracellular IFNγ (FIG. 11A) and IL-17 by $T_H$ cells (FIG. 11B) induced by allogeneic activated DC in an MLR;

FIGS. 12 (A-D) demonstrate docked structures of grassystatins A (1) and C (3) with cathepsins D and E: FIG. 12A shows docked conformation of grassystatin A (1) with cathepsin D; FIG. 12B shows docked conformation of grassystatin A (1) with cathepsin E; FIG. 12C shows docked conformation of grassystatin C (3) with cathepsin D; FIG. 12D shows docked conformation of grassystatin C (3) with cathepsin E.

DETAILED DESCRIPTION OF THE INVENTION

The invention features compounds, compositions, and methods of using such compounds for treating aspartic protease or metalloprotease related diseases or disorders. In certain embodiments, the compounds are novel bioactive compounds that are discovered from the source of marine cyanobacteria. In certain embodiments, the compounds of the invention are natural products and their analogs thereof. In one embodiment, the compounds are useful as selective protease inhibitors.

The invention is based, at least in part, on the discovery of grassystatin A (1) and two natural analogs (i.e., grassystatins B (2) and C (3)) through exploration of marine cyanobacteria as a source of novel bioactive compounds. The structures of grassystatins A (1), B (2) and C (3) were determined using NMR, MS, and chiral HPLC techniques. It was found surprisingly that grassystatins A (1), B (2) and C (3) are capable of selectively inhibiting various proteases (such as, cathepsins D and E, aspartic protease, and metalloprotease).

I. Definitions

Before further description of the present invention, and in order that the invention may be more readily understood, certain terms are first defined and collected here for convenience.

As used in the specification and claims, the singular term "a", "an" and "the" include plural references unless the context clearly dictates otherwise. For example, the term "a cell" includes a plurality of cells, including mixtures thereof. The term "a nucleic acid molecule" includes a plurality of nucleic acid molecules.

The term "administration" or "administering" includes routes of introducing the compound of the invention(s) to a subject to perform their intended function. Examples of routes of administration that may be used include injection (subcutaneous, intravenous, parenterally, intraperitoneally, intrathecal), oral, inhalation, rectal and transdermal. The pharmaceutical preparations may be given by forms suitable for each administration route. For example, these preparations are administered in tablets or capsule form, by injection, inhalation, eye lotion, ointment, suppository, etc. administration by injection, infusion or inhalation; topical by lotion or ointment; and rectal by suppositories. Oral administration is preferred. The injection can be bolus or can be continuous infusion. Depending on the route of administration, the compound of the invention can be coated with or disposed in a selected material to protect it from natural conditions which may detrimentally affect its ability to perform its intended function. The compound of the invention can be administered alone, or in conjunction with either another agent as described above or with a pharmaceutically-acceptable carrier, or both. The compound of the invention can be administered prior to the administration of the other agent, simultaneously with the agent, or after the administration of the agent. Furthermore, the compound of the invention can also be administered in a pro-drug form which is converted into its active metabolite, or more active metabolite in vivo.

The term "agent" is meant a small molecule compound, a polypeptide, polynucleotide, or fragment, or analog thereof, or other biologically active molecule.

The term "amide" or "pharmaceutically acceptable amide" in accordance with the invention refers to derivatives produced by reaction of a carboxylic acid or ester group of a compound of the invention and an amine moiety (e.g., ammonia and alkylamines). Alternatively, the amide derivatives may be produced by a reaction of a carboxylic acid or ester compound and an amine moiety in the compound(s) of the invention. It will be understood that amides of the invention include those that hydrolyze in vivo and those that break down readily in the human body to leave the parent compound or a salt thereof. Examples of amides in accordance with the invention include, for example, primary amides, lower-alkyl amides, di-lower alkyl amides, and hydroxy amides.

The term "aspartic protease-related disease or disorder", as used herein, refers to a disease or disorder caused by or associated with overactivity or overexpression of one or more aspartic proteases. Similarly, the term "gamma secretase-related disease or disorder", as used herein, refers to a disease or disorder caused by or associated with overactivity or overexpression of gamma secretase, and the term "metalloprotease-related disease or disorder", as used herein, refers to a disease or disorder caused by or associated with overactivity or overexpression of one or more metalloproteases.

The term "associating with" refers to a condition of proximity between a chemical entity or compound, or portions thereof, and a binding pocket or binding site on a protein. The association may be non-covalent (wherein the juxtaposition is energetically favored by hydrogen bonding or van der Waals or electrostatic interactions) or it may be covalent.

The term "binding pocket", as used herein, refers to a region of a molecule or molecular complex, that, as a result of its shape, favorably associates with another chemical entity or compound.

The language "biological activities" of a compound of the invention includes all activities elicited by compound of the inventions in a responsive cell. It includes genomic and non-genomic activities elicited by these compounds.

"Biological composition" or "biological sample" refers to a composition containing or derived from cells or biopolymers. Cell-containing compositions include, for example, mammalian blood, red cell concentrates, platelet concentrates, leukocyte concentrates, blood cell proteins, blood plasma, platelet-rich plasma, a plasma concentrate, a precipitate from any fractionation of the plasma, a supernatant from any fractionation of the plasma, blood plasma protein fractions, purified or partially purified blood proteins or other components, serum, semen, mammalian colostrum, milk, saliva, placental extracts, a cryoprecipitate, a cryosupernatant, a cell lysate, mammalian cell culture or culture medium, products of fermentation, ascites fluid, proteins induced in blood cells, and products produced in cell culture by normal or transformed cells (e.g., via recombinant DNA or monoclonal antibody technology). Biological compositions can be cell-free. In one embodiment, a suitable biological composition or biological sample is a red blood cell suspension. In some embodiments, the blood cell suspension includes mammalian blood cells. Preferably, the blood cells are obtained from a human, a non-human primate, a dog, a cat, a horse, a cow, a goat, a sheep or a pig. In certain embodiments, the blood cell suspension includes red blood cells and/or platelets and/or leukocytes and/or bone marrow cells.

The term "chiral" refers to molecules which have the property of non-superimposability of the mirror image partner, while the term "achiral" refers to molecules which are superimposable on their minor image partner.

The terms "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

The term "diastereomers" refers to stereoisomers with two or more centers of dissymmetry and whose molecules are not minor images of one another.

The term "effective amount" includes an amount effective, at dosages and for periods of time necessary, to achieve the desired result, e.g., sufficient to treat a disease or disorder delineated herein. An effective amount of compound of the invention may vary according to factors such as the disease state, age, and weight of the subject, and the ability of the compound of the invention to elicit a desired response in a cell or in the subject. Dosage regimens may be adjusted to provide the optimum therapeutic response. An effective amount is also one in which any toxic or detrimental effects (e.g., side effects) of the compound of the invention are outweighed by the therapeutically beneficial effects.

A therapeutically effective amount of compound (I.e., an effective dosage) may range from about 0.005 μg/kg to about 200 mg/kg, about 0.1 μg/kg to about 100 mg/kg, or about 1 mg/kg to about 50 mg/kg of body weight. In other embodiments, a therapeutically effect concentration may range from about 1.0 nM to about 1 μM. The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a compound can include a single treatment or, preferably, can include a series of treatments. In one example, a subject is treated with a compound in the range of between about 0.005 μg/kg to about 200 mg/kg of body weight, one time per day for between about 1 to 10 weeks, between 2 to 10 weeks, between about 1 to 8 weeks, or for about 4, 5, or 6 weeks. It will also be appreciated that the effective dosage of a compound used for treatment may increase or decrease over the course of a particular treatment.

The term "enantiomers" refers to two stereoisomers of a compound which are non-superimposable mirror images of one another. An equimolar mixture of two enantiomers is called a "racemic mixture" or a "racemate."

The term "ester" or "pharmaceutically acceptable ester" as used herein refers to esterified derivatives (if applicable) of the compounds of the invention. An ester can be prepared, for example, by separately reacting a compound in its free acid form or hydroxyl form with a suitable esterifying agent. Hydroxyl groups can be converted into esters via treatment with a free or activated carboxylic acid. Esters in accordance with the invention include those that hydrolyze in vivo and those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms.

Examples of esters in accordance with the invention include, for example, substituted and unsubstituted, branched or unbranched lower alkyl esters (e.g., propionic acid esters), lower alkenyl esters, di-lower alkyl-amino lower-alkyl esters (e.g., dimethylaminoethyl ester), acylamino lower alkyl esters (e.g., acetyloxymethyl ester), acyloxy lower alkyl esters (e.g., pivaloyloxymethyl ester), aryl esters (phenyl ester), aryl-lower alkyl esters (e.g., benzyl ester), substituted (e.g., with methyl, halo, or methoxy substituents) aryl and aryl-lower alkyl esters. Particular esters of the invention include, but are not limited to, tert-Butyl esters, formates, acetates, propionates, butyrates, acrylates and ethylsuccinates.

The term "hydrate" means a compound of the present invention or a salt thereof, which further includes a stoichiometric or non-stoichiometric amount of water bound by non-covalent intermolecular forces.

The language "improved biological properties" refers to any activity inherent in a compound of the invention that enhances its effectiveness in vivo. In one embodiment, this term refers to any qualitative or quantitative improved therapeutic property of a compound of the invention, such as reduced toxicity.

The term "in combination with" is intended to refer to all forms of administration that provide an a compound of the invention together with an additional pharmaceutical agent, such as a second compound used in clinic for treating or preventing osteoclast-related disease or disorder, where the two are administered concurrently or sequentially in any order.

The terms "isolated," "purified," "pure" or "biologically pure" refer to material that is substantially or essentially free from components (such as proteins, nucleic acids, carbohydrates, and other cellular materials) that normally accompany it as found in its native or natural state, e.g., its state in an organism in which the compound or material naturally occurs. Purity and homogeneity are typically determined using analytical chemistry techniques such as polyacrylamide gel electrophoresis or high performance liquid chromatography. In certain embodiments, a compound of this invention is at least 50% pure, 60% pure, 75% pure, 80% pure, 85% pure, at least 90% pure, or at least 95% pure (e.g., by weight). In certain instances, the compound is at least 98% pure, 99% pure, 99.5% pure, 99.8% pure, or 99.9% pure.

The term "isomers" or "stereoisomers" refers to compounds which have identical chemical constitution, but differ with regard to the arrangement of the atoms or groups in space.

The term "modulate" refers to an increase or decrease, e.g., in the ability of a compound inhibiting activity of a target in response to exposure to a compound of the invention, including for example in an subject (e.g., animal, human) such that a desired end result is achieved, e.g., a therapeutic result.

The term "natural product" as used herein refers to a chemical compound or substance produced by a living organism. In certain embodiments, the term refers to a compound found in nature that usually has a pharmacological or biological activity for use in pharmaceutical drug discovery and drug design. Natural products may be extracted from tissues of terrestrial plants, marine organisms, or microorganism fermentation broths. Most likely, a natural product is present in a mixture of other compounds when extracted from a natural source. To obtain the compound in a pure form, it can be isolated and purified. How a natural product can be isolated and purified depends on factors such as the structure and stability of the compound, as well as on its quantity in the mixture.

The term "obtaining" as in "obtaining a compound" capable of modulating (agonizing, antagonizing) a target delineated herein includes purchasing, synthesizing or otherwise acquiring the compound.

The term "pharmaceutically acceptable salt," is a salt formed from, for example, an acid and a basic group of a compound of any one of the formulae disclosed herein. Illustrative salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, besylate, gentisinate, fumarate, gluconate, glucaronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts. The term "pharmaceutically acceptable salt" also refers to a salt prepared from a compound of any one of the formulae disclosed herein having an acidic functional group, such as a carboxylic acid functional group, and a pharmaceutically acceptable inorganic or organic base. Suitable bases include, but are not limited to, hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy-substituted mono-, di-, or trialkylamines; dicyclohexylamine; tributyl amine; pyridine; N-methyl,N-ethylamine; diethylamine; triethylamine; mono-, bis-, or tris-(2-hydroxy-lower alkyl amines), such as mono-, bis-, or tris-(2-hydroxyethyl)amine, 2-hydroxy-tert-butylamine, or tris-(hydroxymethyl)methylamine, N,N,-di-lower alkyl-N-(hydroxy lower alkyl)-amines, such as N,N-dimethyl-N-(2-hydroxyethyl)amine, or tri-(2-hydroxyethyl)amine; N-methyl-D-glucamine; and amino acids such as arginine, lysine, and the like. The term "pharmaceutically acceptable salt" also refers to a salt prepared from a compound of any one of the formulae disclosed herein having a basic functional group, such as an amino functional group, and a pharmaceutically acceptable inorganic or organic acid. Suitable acids include hydrogen sulfate, citric acid, acetic acid, oxalic acid, hydrochloric acid (HCl), hydrogen bromide (HBr), hydrogen iodide (HI), nitric acid, hydrogen bisulfide, phosphoric acid, lactic acid, salicylic acid, tartaric acid, bitartratic acid, ascorbic acid, succinic acid, maleic acid, besylic acid, fumaric acid, gluconic acid, glucaronic acid, formic acid, benzoic acid, glutamic acid, methanesulfonic acid, ethanesulfonic acid, benzenesulfonic acid, and p-toluenesulfonic acid.

The term "polymorph" means solid crystalline forms of a compound of the present invention or complex thereof. Different polymorphs of the same compound can exhibit different physical, chemical and/or spectroscopic properties. Different physical properties include, but are not limited to stability (e.g., to heat or light), compressibility and density (important in formulation and product manufacturing), and dissolution rates (which can affect bioavailability). Differences in stability can result from changes in chemical reactivity (e.g., differential oxidation, such that a dosage form discolors more rapidly when comprised of one polymorph than when comprised of another polymorph) or mechanical characteristics (e.g., tablets crumble on storage as a kinetically favored polymorph converts to thermodynamically more stable polymorph) or both (e.g., tablets of one polymorph are more susceptible to breakdown at high humidity). Different physical properties of polymorphs can affect their processing. For example, one polymorph might be more likely to form solvates or might be more difficult to filter or wash free of impurities than another due to, for example, the shape or size distribution of particles of it.

The term "prodrug" or "pro-drug" includes compounds with moieties that can be metabolized in vivo. Generally, the prodrugs are metabolized in vivo by esterases or by other mechanisms to active drugs. Examples of prodrugs and their uses are well known in the art (See, e.g., Berge et al. (1977) "Pharmaceutical Salts", *J. Pharm. Sci.* 66:1-19). The prodrugs can be prepared in situ during the final isolation and purification of the compounds, or by separately reacting the purified compound in its free acid form or hydroxyl with a suitable esterifying agent. Hydroxyl groups can be converted into esters via treatment with a carboxylic acid. Examples of prodrug moieties include substituted and unsubstituted, branch or unbranched lower alkyl ester moieties, (e.g., propionoic acid esters), lower alkenyl esters, di-lower alkylamino lower-alkyl esters (e.g., dimethylaminoethyl ester), acylamino lower alkyl esters (e.g., acetyloxymethyl ester), acyloxy lower alkyl esters (e.g., pivaloyloxymethyl ester), aryl esters (phenyl ester), aryl-lower alkyl esters (e.g., benzyl ester), substituted (e.g., with methyl, halo, or methoxy substituents) aryl and aryl-lower alkyl esters, amides, lower-alkyl amides, di-lower alkyl amides, and hydroxy amides. Preferred prodrug moieties are propionoic acid esters and acyl esters. Prodrugs which are converted to active forms through other mechanisms in vivo are also included.

The language "a prophylactically effective amount" of a compound refers to an amount of a compound of the invention or otherwise described herein which is effective, upon single or multiple dose administration to the patient, in preventing or treating a disorder herein.

The term "subject" includes organisms which are capable of suffering from a disorder as described herein or who could otherwise benefit from the administration of a compound of the present invention, such as human and non-human animals. Preferred humans include human patients suffering from or prone to suffering from diseases or disorders as discussed above, as described herein. The term "non-human animals" of the invention includes all vertebrates, e.g., mammals, e.g., rodents, e.g., mice, and non-mammals, such as non-human primates, e.g., sheep, dog, cow, chickens, amphibians, reptiles, etc. A "subject identified as being in need of treatment" includes a subject diagnosed, e.g., by a medical or veterinary professional, as suffering from or susceptible to a disease, disorder or condition described herein.

The phrases "systemic administration," "administered systemically", "peripheral administration" and "administered peripherally" as used herein mean the administration of a compound of the invention(s), drug or other material, such that it enters the patient's system and, thus, is subject to metabolism and other like processes, for example, subcutaneous administration.

With respect to the nomenclature of a chiral center, terms "d" and "l" configuration are as defined by the IUPAC Recommendations. As to the use of the terms, diastereomer, racemate, epimer and enantiomer is used in their normal context to describe the stereochemistry of preparations.

II. Compounds of the Invention

In one aspect, the invention provides novel bioactive compounds. In one embodiment, the compounds of the invention are capable of selectively inhibiting proteases. In another embodiment, the compounds are capable of inhibiting enzymes, including human enzymes, such as gamma secretase, cathepsins D and E, aspartic proteases, or metalloproteases. In one embodiment, the invention provides compounds capable of inhibiting aspartic proteases or metalloproteases selectively. In certain embodiments, the compounds are capable of inhibiting cathepsin D and/or cathepsin E selectively. In certain embodiments, the compounds of the invention are capable of inhibiting gamma secretase.

In certain embodiments, the compounds of the invention are isolated or purified natural products, and/or natural analogs thereof. In one embodiment, the compounds are isolated or purified natural products produced by marine cyanobacteria.

Marine cyanobacteria are known to produce a vast array of secondary metabolites. Cyanobacteria produce modified peptides through the non-ribosomal peptide synthetase (NRPS) pathway or through combinations of the NRPS and polyketide synthase (PKS) pathways (see Dittman et al., Appl. Microbiol. Biotechnol. 2001, 57, 467-473). Both of these pathways are highly modular, presumably allowing evolution of bioactive compounds through combinatorial alterations.

In one embodiment, the compounds are at least 85% pure. Other embodiments provide that the compounds are at least 90%, 95%, or 99% pure. In one embodiment, the compound of the invention is selected from the group of grassystatins A (Compound 1), B (Compound 2), and C (Compound 3), with structures demonstrated as follows:

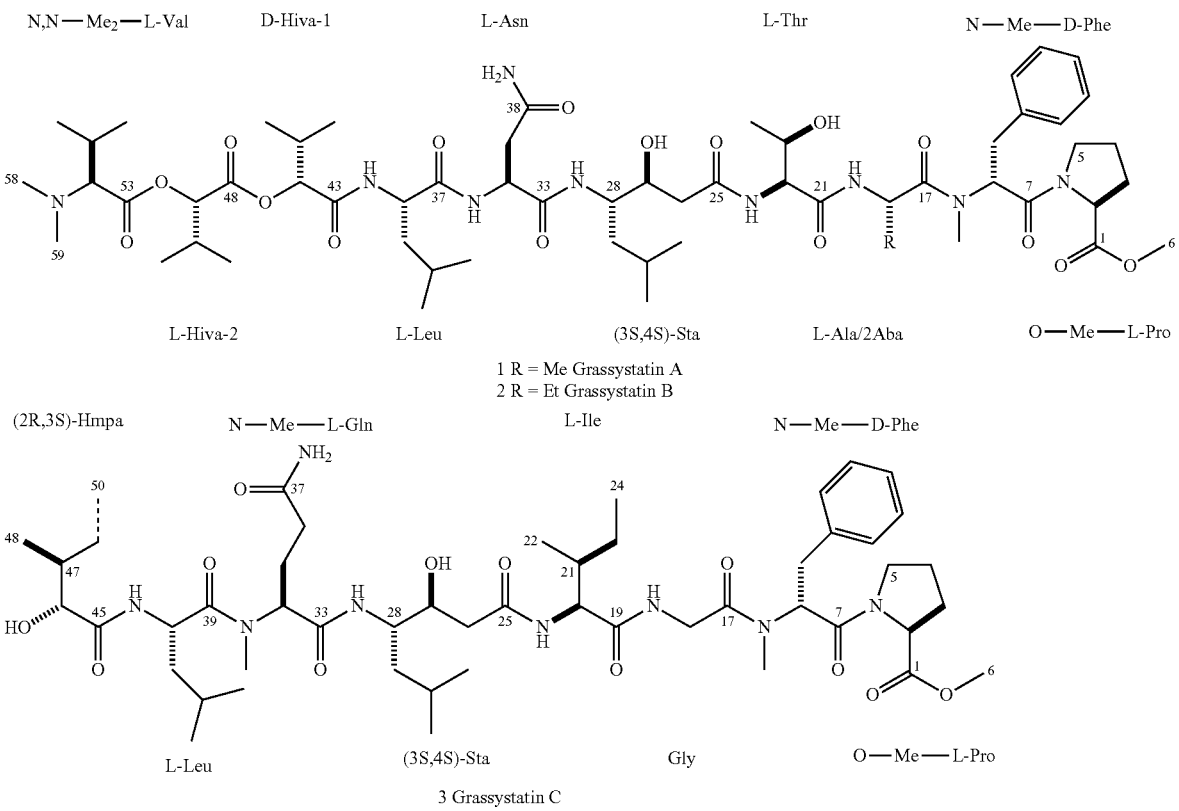

The invention also relates to a pharmaceutically acceptable salt, ester, amide, hydrate, stereoisomer, or solvate thereof, of the compounds mentioned herein.

It is noted that grassystatins A-C (1-3) contain a statine unit [(3S,4S)-4-amino-3-hydroxy-6-methylheptanoic acid, Sta.], which was first described in the broad-spectrum natural aspartic protease inhibitor pepstatin A (Morishima et al. *J. Antibiot.* 1970, 23, 263-265; and Umezawa et al. *J. Antibiot.* 1970, 23, 259-262). It was reported that statine arises from a mixed NRPS/PKS pathway that condenses leucine and malonate units (Morishima et al., *J. Antibiot.* 1974, 27, 267-273) The structural relatives among cyanobacterial natural products are tasiamide and tasiamide B (FIG. 4) (Williams et al., *J. Nat. Prod.* 2002, 65, 1336-1339; and Williams et al. *J. Nat. Prod.* 2003, 66, 1006-1009). Tasiamide does not contain a statine unit and there are also some differences in configuration of several amino acid residues (FIG. 4).

Further, the compounds of this invention may contain one or more asymmetric centers and thus occur as racemates and racemic mixtures, single enantiomers, individual diastereomers and diastereomeric mixtures. All such isomeric forms of the compounds are also expressly included in the invention. The compounds of the invention may also be represented in multiple tautomeric forms, in such instances, the invention expressly includes all tautomeric forms of the compounds described herein. All such isomeric forms of such compounds are expressly included in the present invention. In certain instances, the purity of a compound of the invention may refer to the purity of the compound in a single isomeric form. In other instances, the purity of a compound may refer to the purity of the compound in all isomeric forms. Moreover, all crystal forms of the compounds described herein are expressly included in the invention.

Naturally occurring or synthetic isomers can be separated in several ways known in the art. Methods for separating a racemic mixture of two enantiomers include chromatography using a chiral stationary phase (see, e.g., "Chiral Liquid Chromatography," W. J. Lough, Ed. Chapman and Hall, New York (1989)). Enantiomers can also be separated by classical resolution techniques. For example, formation of diastereomeric salts and fractional crystallization can be used to separate enantiomers. For the separation of enantiomers of carboxylic acids, the diastereomeric salts can be formed by addition of enantiomerically pure chiral bases such as brucine, quinine, ephedrine, strychnine, and the like. Alternatively, diastereomeric esters can be formed with enantiomerically pure chiral alcohols such as menthol, followed by separation of the diastereomeric esters and hydrolysis to yield the free, enantiomerically enriched carboxylic acid. For separation of the optical isomers of amino compounds, addition of chiral carboxylic or sulfonic acids, such as camphorsulfonic acid, tartaric acid, mandelic acid, or lactic acid can result in formation of the diastereomeric salts.

Methods of isolation, purification, and structural determination of the compounds of the invention are described in detail infra.

III. Uses and Methods of the Invention

In one aspect, the invention provides a method for treating an aspartic protease-related disease or disorder in a subject (e.g., a subject identified as being in need of such treatment). The method includes administering to the subject an effective amount of a compound of the invention. In certain embodiment, the disease or disorder is related to cathepsin D. In other embodiments, the disease or disorder is related to cathepsin E. In one embodiment, the disease or disorder is a breast cancer. In another embodiment, the disease or disorder is Alzheimer's disease.

Cathepsins are a family of proteases that are found in many types of cells. The cathepsin family includes approximately a dozen members, which are distinguished by their structure, catalytic mechanism, and the types of proteins they cleave. Cathepsin D, a member of the cathepsin family, is an aspartic protease. It is believed that cathepsin D is involved in the pathogenesis of several diseases, including breast cancer and Alzheimer's disease.

Cathepsin E, another member of the family, is a member of the peptidase C1 family, has a specificity similar to that of pepsin A and cathepsin D. It is an intracellular proteinase that does not appear to be involved in the digestion of dietary protein and is found in highest concentration in the surface of epithelial mucus-producing cells of the stomach. It is an aspartic proteinase found in more than half of gastric cancers.

In another aspect, the invention provides a method of treating a metalloprotease-related disease or disorder in a subject (e.g., a subject identified as being in need of such treatment). The method includes administering to the subject an effective amount of a compound of the invention. In one embodiment, the metalloprotease related disease or disorder is a TACE (tumor necrosis factor (TNF)-converting enzyme) related disease or disorder.

Metalloproteases are a group of proteases. They are proteolytic enzymes whose catalytic mechanism involves a metal (such as zinc and cobalt). TACE is an ADAM protease to process the known physiological substrate and inflammatory cytokine, membrane-bound precursor-TNF-α, to its mature soluble form. TACE has been found as required for several different processing events, such as tumor growth factor-α (TGF-α) precursor and amyloid precursor protein (APP) cleavage (see, e.g., Drug Discovery Today, vol 6, Issue 8, 1 Apr. 2001, Pages 417-426).

The invention also provides a method of treating a disease or disorder selected from the group consisting of disorders of blood coagulation, disorder of the cell cycle, infection, neurodegenerative disorders, autoimmune disorders, allergic diseases, cancer, HIV infection, AIDS, Alzheimer's disease, transplant rejection, and intracellular pathogen related diseases. The method includes administering to a subject (e.g., a subject identified as being in need of such treatment) an effective amount of a compound of the invention. In certain embodiments, the disease or disorder being treated is rheumatoid arthritis or asthma.

Another aspect of the invention provides a method of inhibiting T-cell proliferation in a subject. The method includes administering to the subject an effective amount of a compound of the invention.

T-cell (or T lymphocyte) belong to a group of white blood cells (known as lymphocytes) that play a central role in cell-mediated immunity. T-cell has a special receptor on its cell surface called T-cell receptor (TCR). Several different subsets of T cells (such as, $T_H$ cells, $T_c$ cells, gamma delta T cells, $T_{reg}$ cells, and NKT cells) have been discovered so far.

In addition, the invention also provides a method of reducing IL-17 production by using an effective amount of a compound of the invention. The method is applicable either in a subject or in a cell.

IL-17 (or Interleukin-17) belongs to a group of cytokines (IL-17 family). IL-17 was identified as a transcript from a rodent T-cell hybridoma (see Rouvier et al., *J. Immunol.* 150 (12): 5445-56). IL-17 shows high homology to viral IL-17 encoded by an open reading frame of the T lymphotropic rhadinovirus Herpesvirus saimiri (see Rouvier et al.). IL-17 may be expressed in the organisms, such as, kidney, pancreas, liver, fibroblast, lung, brain, and intestine (see, e.g., Kolls et al. *Immunity* 21 (4), 2004, 467-76).

Moreover, the invention also provides a method of reducing IFN-γ production in a subject or in a cell. The method comprises administering to the subject or the cell an effective amount of a compound of the invention.

IFN-γ (or type II interferon) is a cytokine that is critical for innate and adaptive immunity against viral and intracellular bacterial infections and for tumor control. Aberrant IFN-γ expression is associated with autoinflammatory and autoimmune diseases. IFN-γ plays an important role in the immune systems. It is believed that IFN-γ is produced predominantly by natural killer (NK) and natural killer T cells as part of the innate immune response, and by CD4 and CD8 cytotoxic T lymphocyte effector T cells once antigen-specific immunity develops (see. e.g, Schoenborn et al., *Adv. Immunol.* 2007, 96: 41-101).

In another aspect, the invention provides a method of inhibiting cathepsin D by contacting cathepsin D in vivo or in vitro with a compound of the invention. In still another aspect, the invention provides a method of inhibiting cathepsin E by contacting cathepsin E protease in vivo or in vitro with a compound of the invention.

The invention also provides a method of inhibiting gamma secretase by contacting a gamma secretase in vivo or in vitro with a compound of the invention.

Gamma secretase is a multi-subunit protease complex that cleaves single-pass transmembrane proteins at residues within the transmembrane domain. A substrate of gamma secretase is amyloid precursor protein, which, when cleaved by both gamma and beta secretase, produces an amino acid peptide called amyloid beta, which is the primary component of amyloid plaques found in the brains of Alzheimer's disease patients. Gamma secretase is also critical in the related processing of the Notch protein.

In another aspect, the invention provides a method of treating a gamma secretase-related disease or disorder in a subject (e.g., a subject identified as being in need of such treatment). The method includes administering an effective amount of a compound of the invention to the subject, thereby treating the gamma secretase-related disease or disorder. In one embodiment, the gamma secretase-related disease or disorder is Alzheimer's disease.

In certain embodiments, a compound of the invention in accordance with any of the methods and uses described supra. is administered at a dosage other than a dosage that is required for showing optimum effects in a subject. Determination of an effective dosage of a specific compound can be readily made by the physician or veterinarian (the "attending clinician"), as one skilled in the art, by the use of known techniques or by following medical protocols.

Methods delineated herein include those wherein the subject is identified as in need of a particular stated treatment. Identifying a subject in need of such treatment can be in the judgment of a subject or a health care professional and can be subjective (e.g. opinion) or objective (e.g. measurable by a test or diagnostic method). In other methods, the subject is prescreened or identified as in need of such treatment by assessment for a relevant marker or indicator of suitability for such treatment.

In certain embodiments, the compound of the invention can be used in combination therapy with existing drug(s) to treat the diseases, disorders or symptoms as above discussed.

Other existing drugs to treat the diseases or disorders herein that may be used can be found in *Harrison's Principles of Internal Medicine*, Thirteenth Edition, Eds. T. R. Harrison et al. McGraw-Hill N.Y., NY; and the Physicians Desk Reference 62th Edition 2008, Oradell New Jersey, Medical Economics Co., the complete contents of which are expressly incorporated herein by reference. The compound of the invention and the suitable existing drug(s) may be administered to a subject in the same pharmaceutical composition or in different pharmaceutical compositions (at the same time or at different times).

Determination of a therapeutically effective amount or a prophylactically effective amount of the compound of the invention can be readily made by the physician or veterinarian (the "attending clinician"), as one skilled in the art, by the use of known techniques and by observing results obtained under analogous circumstances. The dosages may be varied depending upon the requirements of the subject being treated in the judgment of the attending clinician; the severity of the condition being treated and the particular compound being employed. In determining the therapeutically effective amount or dose, and the prophylactically effective amount or dose, a number of factors are considered by the attending clinician, including, but not limited to: the specific disease involved; pharmacodynamic characteristics of the particular agent and its mode and route of administration; the desired time course of treatment; the species of mammal; its size, age, and general health; the specific disease involved; the degree of or involvement or the severity of the disease; the response of the individual patient; the particular compound administered; the mode of administration; the bioavailability characteristics of the preparation administered; the dose regimen selected; the kind of concurrent treatment (i.e., the interaction of the compound of the invention with other co-administered therapeutics); and other relevant circumstances.

Treatment can be initiated with smaller dosages, which are less than the optimum dose of the compound. Thereafter, the dosage may be increased by small increments until the optimum effect under the circumstances is reached. For convenience, the total daily dosage may be divided and administered in portions during the day if desired. A therapeutically effective amount and a prophylactically effective amount of a compound of the invention is expected to vary from about 0.005 µg/kg to about 200 mg/kg per day, or 0.001 milligram per kilogram of body weight per day (mg/kg/day) to about 100 mg/kg/day.

Compounds determined to be effective for the prevention or treatment of the diseases or disorders herein in a subject, e.g., dogs, chickens, and rodents, may also be useful in treatment of the diseases or disorders in humans. Those skilled in the art of treating the diseases or disorders in humans will know, based upon the data obtained in animal studies, the dosage and route of administration of the compound to humans.

The identification of a subject in need for treatment is well within the ability and knowledge of one skilled in the art. Certain of the methods for identification of a subject the disease/disorder herein or who are at risk of developing such a disease/disorder which can be treated by the subject method are appreciated in the medical arts, such as family history, and the presence of risk factors associated with the development of that disease state in the patient. A clinician skilled in the art can readily identify such candidate patients, by the use of, for example, clinical tests, physical examination and medical/family history.

A method of assessing the efficacy of a treatment in a subject includes determining the pre-treatment extent of the disease/disorder by methods well known in the art and then administering to the subject a therapeutically effective amount of a compound according to the invention. After an appropriate period of time after the administration of the compound (e.g., 1 day, 1 week, 2 weeks, one month, six months), the extent and the severity of the disease/disorder are determined again. The modulation (e.g., decrease) of the extent or severity of the disease or disorder indicates efficacy of the treatment. The extent or severity of the disease or disorder may be determined periodically throughout treatment.

The methods and uses of the invention can be performed on cells in culture, e.g. in vitro or ex vivo, or on cells present in an animal subject, e.g., in vivo. Compounds of the inventions can be initially tested in vitro using primary cultures of cells and the like. Compound of the invention can be initially tested in vitro using cells or other mammalian or non-mammalian animal models. Alternatively, the effects of compound of the invention can be characterized in vivo using animals models.

Further, the invention also provides the use of a compound of the invention, alone or together with one or more additional therapeutic agents in the manufacture of a medicament, either as a single composition or as separate dosage forms, for treatment in a subject of a disease, disorder or symptom set forth herein. Another aspect of the invention is a compound of the present invention for use in the treatment or prevention in a subject of a disease, disorder or symptom thereof delineated herein.

IV. Exaction, Isolation and Structural Determination Of the Compounds

In one embodiment, the compounds of the invention are natural products, and/or natural analogs thereof. As discussed above, natural products are chemical compounds or substances produced by a living organism. The sources of natural products include, for example, tissues of terrestrial plants, marine organisms, and microorganism fermentation broths. In most circumstances, a crude mixture is first extracted from any one of these sources. It may be followed by one or more steps of fractionation, isolation and/or purification on the crude extract to obtain a natural product in its isolated and/or pure state.

An extraction procedure may be chosen depending on the nature of the source and the compounds to be isolated. Prior to choosing a method, it is necessary to know what type of the target needs to be extracted, such as, an unknown or known compound, a group of structurally related compounds, or secondary metabolites produced by the natural source etc. Further, the extraction process, may be determined by the nature of the source as well, such as, plant materials, animal sample, and microorganism).

Extraction methods may include, but are not limited to, maceration, boiling, soxhlet, supercritical fluid extraction, sublimation, and steam distillation. Further, different types of solvents may be used in an extraction process. For polar extraction, the solvents can be, for example, water, ethanol, and methanol (MeOH). For medium polarity extraction, solvents such as, ethyl acetate (EtOAc), and dichloromethane (DCM) may be used. For nonpolar extraction, n-hexane, pet-ether, and chloroform ($CHCl_3$) may be used (see Sarker et al., Natural Product Isolation: An Overview, Methods in Biotechnology, 20, 2005, 1-25).

A crude natural product extract is a mixture of compounds and other substances. The crude extract is usually separated into various fractions through fractionation using liquid-liquid extraction or a chromatographic technologies, such as, vacuum liquid chromatography (VLC), column chromatography (CC), size-exclusion chromatography (SEC), solid-phase extraction (SPE), high-performance thin-layer chromatography (HPTLC), multiflash chromatography, and chromatotron etc. In certain embodiments, fractionation is guided by a detection technique, such as, ultraviolet (UV), or high-performance liquid chromatography (HPLC) (see Sarker et al., Natural Product Isolation: An Overview, Methods in Biotechnology, 20, 2005, 1-25).

Various isolation protocols may be used depending on the nature of the target compound present in the crude extracts or fractions. The natures of the molecule needs to be considered include for example, solubility (hydrophobicity or hydrophilicity), acid-base properties, charge, stability, and molecular size. In certain instances, qualitative tests for the presence of various types of compounds are performed together with analytical thin-layer chromatography (TLC) or HPLC profiling. Further, the nature of the extract can also be helpful for choosing the right isolation protocol (see Sarker et al., Natural Product Isolation: An Overview, Methods in Biotechnology, 20, 2005, 1-25).

In certain instances, an isolation protocol may be optimized. Methods for optimizing conditions for isolation, if necessary minimizing competing by-products, are also discussed, and certain aspects can be found in the art. The methods may also additionally include steps, either before or after the steps described specifically herein, to add or remove suitable protecting groups in order to ultimately allow synthesis of the compounds herein. In addition, various synthetic steps may be performed in an alternate sequence or order to give the desired compounds. Synthetic chemistry transformations and protecting group methodologies (protection and deprotection) useful in synthesizing the applicable compounds are known in the art and include, for example, those described in R. Larock, *Comprehensive Organic Transformations*, VCH Publishers (1989); T. W. Greene and P. G. M. Wuts, *Protective Groups in Organic Synthesis*, $3^{rd}$ Ed., John Wiley and Sons (1999); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995) and subsequent editions thereof.

An isolated compound may be identified through structure elucidation. The techniques that are generally used for the structure elucidation include, but are not limited to, Ultraviolet-visible spectroscopy (UV-vis), Infrared spectroscopy (IR), Mass spectrometry (MS), one-dimensional NMR (such as, $^1HNMR$, $^{13}CNMR$, $^{13}CDEPT$, $^{13}CPENDANT$, $^{13}C$ J mod., nOe-diff.), and two-dimensional NMR ($^1H$-$^1H$ COSY, $^1H$-$^1H$ DQF-COSY, $^1H$-$^1H$ COSY-1r, $^1H$-$^1H$ NOESY, $^1H$-$^1H$ ROESY, $^1H$-$^1H$ TOCSY (or HOHAHA), $^1H$-$^{13}C$ HMBC, $^1H$-$^{13}C$ HMQC, $^1H$-$^{13}C$ HSQC, HSQC-TOCSY). Further, X-ray crystallographic techniques may offer information on the optical activity of the compounds.

In certain instances, chemical, biological, or physical assays are also helpful in the extraction, isolation and structural elucidation of the target compound. Applicable assays have been discussed, and can be found in the art.

V. Pharmaceutical Compositions and Kits

The invention also provides a pharmaceutical composition, comprising an effective amount of a compound of the present invention and a pharmaceutically acceptable carrier. In certain embodiments, the compound of the invention can be an isolated or purified compound as described herein, or a pharmaceutically acceptable salt, ester, amide, hydrate, stereoisomer, or solvate thereof. In a further embodiment, the effective amount is effective for treating or preventing a disease or disorder in a subject, as described previously.

The invention also includes kits for treating or preventing the disease or disorder as above discussed. The kit may include a compound of the invention, for example, a compound described herein, pharmaceutically acceptable esters, salts, amides, hydrates, solvates, or stereoisomers thereof, and instructions for use. The instructions for use may include information on dosage, method of delivery, storage of the kit, etc. The kits may also include, reagents, for example, test compounds, buffers, media (e.g., cell growth media), cells, etc. Test compounds may include known compounds or newly discovered compounds, for example, combinatorial libraries of compounds. One or more of the kits of the invention may be packaged together, for example, a kit for assessing the efficacy of an disease treatment may be packaged with a kit for monitoring the progress of a subject being treated according to the invention.

In an embodiment, the compound of the invention is administered to a subject with a need using a pharmaceutically-acceptable formulation, e.g., a pharmaceutically-acceptable formulation that provides sustained delivery of the compound of the invention to a subject for at least 12 hours, 24 hours, 36 hours, 48 hours, one week, two weeks, three weeks, or four weeks after the pharmaceutically-acceptable formulation is administered to the subject.

In certain embodiments, these pharmaceutical compositions are suitable for topical or oral administration to a subject In other embodiments, as described in detail below, the pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, pastes; (2) parenteral administration, for example, by subcutaneous, intramuscular or intravenous injection as, for example, a sterile solution or suspension; (3) topical application, for example, as a cream, ointment or spray applied to the skin; (4) intravaginally or intrarectally, for example, as a pessary, cream or foam; or (5) aerosol, for example, as an aqueous aerosol, liposomal preparation or solid particles containing the compound.

The phrase "pharmaceutically acceptable" refers to those compound of the present invention, compositions containing such compounds, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" includes pharmaceutically-acceptable material, composition or vehicle, such as a liquid or solid filler, diluent, excipient, solvent or encapsulating material, involved in carrying or transporting the subject chemical from one organ, or portion of the body, to another organ, or portion of the body. Each carrier is "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; ($1_3$) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Compositions containing a compound of the invention include those suitable for oral, nasal, topical (including buccal and sublingual), rectal, vaginal, aerosol and/or parenteral administration. The compositions may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred percent, this amount will range from about 1 percent to about ninety-nine percent of active ingredient, from about 5 percent to about 70 percent, or from about 10 percent to about 30 percent.

Methods of preparing these compositions include the step of bringing into association a compound of the invention with the carrier and, optionally, one or more accessory ingredients. In general, the formulations are prepared by uniformly and intimately bringing into association a compound of the invention with liquid carriers, or finely divided solid carriers, or both, and then, if necessary, shaping the product.

Compositions of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the invention as an active ingredient. A compound may also be administered as a bolus, electuary or paste.

In solid dosage forms of the invention for oral administration (capsules, tablets, pills, dragees, powders, granules and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered active ingredient moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compound of the invention include pharmaceutically-acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

In addition to inert diluents, the oral compositions can include adjuvants such as wetting agents, emulsifying and suspending agents, sweetening, flavoring, coloring, perfuming and preservative agents.

Suspensions, in addition to the active compound of the invention(s) may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Pharmaceutical compositions of the invention for rectal or vaginal administration may be presented as a suppository, which may be prepared by mixing one or more compound of the invention(s) with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active agent.

Compositions of the present invention which are suitable for vaginal administration also include pessaries, tampons, creams, gels, pastes, foams or spray formulations containing such carriers as are known in the art to be appropriate.

Dosage forms for the topical or transdermal administration of a compound of the invention(s) include powders, sprays, ointments, pastes, creams, lotions, gels, solutions, patches and inhalants. The active compound of the invention(s) may be mixed under sterile conditions with a pharmaceutically-acceptable carrier, and with any preservatives, buffers, or propellants which may be required.

The ointments, pastes, creams and gels may contain, in addition to compound of the invention(s) of the present invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of the invention(s), excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

The compound of the invention(s) can be alternatively administered by aerosol. This is accomplished by preparing an aqueous aerosol, liposomal preparation or solid particles containing the compound. A nonaqueous (e.g., fluorocarbon propellant) suspension could be used. Sonic nebulizers are preferred because they minimize exposing the agent to shear, which can result in degradation of the compound.

Ordinarily, an aqueous aerosol is made by formulating an aqueous solution or suspension of the agent together with conventional pharmaceutically-acceptable carriers and stabilizers. The carriers and stabilizers vary with the requirements of the particular compound, but typically include nonionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Transdermal patches have the added advantage of providing controlled delivery of a compound of the invention(s) to the body. Such dosage forms can be made by dissolving or dispersing the agent in the proper medium. Absorption enhancers can also be used to increase the flux of the active ingredient across the skin. The rate of such flux can be controlled by either providing a rate controlling membrane or dispersing the active ingredient in a polymer matrix or gel.

Ophthalmic formulations, eye ointments, powders, solutions and the like, are also contemplated as being within the scope of the invention.

Pharmaceutical compositions of the invention suitable for parenteral administration comprise one or more compound of the invention(s) in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers, which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of a compound of the invention in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

When the compounds of the invention are administered as pharmaceuticals, to humans and animals, they can be given per se or as a pharmaceutical composition containing, for example, 0.1 to 99.5% (or 0.5 to 90%) of active ingredient in combination with a pharmaceutically-acceptable carrier.

Regardless of the route of administration selected, the compound of the invention, which may be used in a suitable hydrated form, and/or the pharmaceutical compositions of the present invention, are formulated into pharmaceutically-acceptable dosage forms by conventional methods known to those of skill in the art.

VI. Examples

The following examples are provided by way of illustration and are not intended to limit the scope of the invention.

General Experimental Procedures:

Optical rotation was measured on a Perkin-Elmer 341 polarimeter. UV was measured on a SpectraMax M5 (Molecular Devices) and IR data obtained on a Bruker Vector 22 instrument. $^1$H and 2D NMR spectra in CDCl$_3$ for compounds 1 and 2 were recorded on a Bruker 500 MHz spectrometer. $^{13}$C and APT spectra for compound 1 were recorded on a Bruker 600 MHz Avance Spectrometer. $^1$H and 2D NMR spectra in CDCl$_3$ for compound 3, and also $^1$H and 2D NMR spectra in DMSO-d$_6$ for compound 1 were collected on a Bruker Avance II 600 MHz spectrometer using a 1-mm triple-resonance high-temperature superconducting cryogenic probe (see Brey et al., construction, and validation of a 1-mm triple-resonance high-temperature-superconducting probe for NMR. *J. Magn. Reson.* 2006, 179, 290-293).

Spectra were referenced to residual solvent signals [$\delta_{H/C}$ 7.26/77.0 (CDCl$_3$) and $\delta_{H/C}$ 2.49/39.5 (DMSO-d$_6$)]. HMQC and HSQC experiments were optimized for 145 Hz, and HMBC experiments were optimized for 7 Hz. HRESI/APCIMS data were recorded on an Agilent LC-TOF mass spectrometer equipped with an APCI/ESI multimode ion source detector in positive ion mode. LC-MS data were obtained using an API 3200 (Applied Biosystems) equipped with a Shimadzu LC system. ESIMS fragmentation data were obtained on an API 3200 by direct injection with a syringe driver. Flow cytometry was carried out on a FACSCalibur flow cytometer using CellQuest software (BD Biosciences, Heidelberg, Germany). Figures of docked ligands were prepared using PyMol.

Example 1

Extraction and Isolation

Samples of the cyanobacterium, identified as *Lyngbya confervoides*, were collected off Grassy Key and then fractionated in accordance with the previously described methods (see, e.g., Kwan et al., Total structure determination of grassypeptolide, a new marine cyanobacterial cytotoxin. *Org. Lett* 2008, 10, 789-792). The non-polar extract (MeOH-EtOAc 1:1) of each collection was subjected to silica chromatography. The silica gel fraction eluting with 100% methanol was purified by preparative reversed-phase HPLC (Phenomenex Luna 10u C$_{18}$ AXI, 100×21.2 mm, 10.0 mL/min; UV detection at 220 and 254 nm), using a MeOH—H$_2$O linear gradient (60-100% over 30 min, then 100% MeOH for 10 min), to give impure grassystatins A (compound 1) and B (compound 2) at t$_R$ 24.3 and 24.9 min, respectively. The impure compounds were then purified using a different column (Phenomenex Ultracarb 5u ODS (30), 250× 10.0 mm, 2.0 mL/min; UV detection at 220 and 254 nm) using the same linear gradient to furnish compound 1, t$_R$ 33.8 min (5.7 mg), and compound 2, t$_R$ 35.1 min (1.3 mg).

Samples of *Lyngbya confervoides* were collected off Key Largo. A voucher specimen is maintained at the Smithsonian Marine Station. The freeze-dried organism was extracted with EtOAc-MeOH (1:1) to afford a non-polar extract, which was directly fractionated by silica gel column and eluted with increasing concentrations of isopropanol in CH$_2$Cl$_2$. The fraction eluting with 100% isopropanol (665.8 mg) was subjected to preparative reversed-phase HPLC [column, Luna C18(2) 100A AXI, 10 µm (100×21.20 mm), Phenomenex; flow rate 10.0 mL/min; detection by UV at 220 and 254 nm] using a linear MeOH—H$_2$O gradient (60-100% MeOH over 30 min, then 100% MeOH for 5 min). A minor peak eluted at t$_R$ 17.2 min, which was then deconvoluted using different conditions [column, ODS-AQ (10×250 mm), YMC; flow rate, 2.0 mL/min; detection by UV at 220 and 254 nm] using the same linear MeOH—H$_2$O gradient, to furnish pure grassystatin C (compound 3) at t$_R$ 27.3 min (1.0 mg).

Example 2

Acid Hydrolysis and Chiral Amino Acid Analysis

A sample of compound 1 (100 µg) was treated with 6 N HCl at 110° C. for 24 h. The hydrolysate was concentrated to dryness, reconstituted in 100 µL H$_2$O and then analyzed by chiral HPLC [column, Chirobiotic TAG (4.6×250 mm), Supelco; solvent, MeOH-10 mM NH$_4$OAc (40:60, pH 5.23): flow rate, 0.5 mL/min; detection by ESIMS in positive ion mode (MRM scan)]. L-Thr, L-Leu, L-Pro, N,N-Me$_2$-L-Val and N-Me-D-Phe eluted at t$_R$ 7.2, 9.0, 14.4, 27.0 and 45.4 min, respectively. The retention times (t$_R$, min; MRM ion pair, parent→product) of the authentic amino acids were as follows: L-Thr (7.2; 120→74), L-allo-Thr (7.5), D-Thr (8.6), D-allo-Thr (11.9), L-Pro (14.4; 116→70), D-Pro (39.5), L-Leu (9.0; 132→86), D-Leu (20.6), N-Me-L-Phe (25.0; 180→134), N-Me-D-Phe (45.4), N,N-Me$_2$-L-Val (27.0; 146→100), and N,N-Me$_2$-D-Val (69.8). The assignment of L-Thr was confirmed by co-injection of the hydrolysate with L-allo-Thr and L-Thr. The MS parameters used were as follows: DP 31.0, EP 8.0, CE 17.3, CXP 3.1, CUR 35, CAD Medium, IS 4500, TEM 750, GS1 65, GS2 65. L-Ala was also detected in positive ion mode, at $t_R$ 8.0, but with slightly different MS conditions. The retention times ($t_R$, min; MRM ion pair, parent→product) of the authentic standards were as follows: L-Ala (8.0; 90-44), D-Ala (14.6). The MS parameters used were as follows: DP 21.0, EP 8.0, CE 15.0, CXP 5.0, CUR 50, CAD Medium, IS 4500, TEM 750, GS1 65, GS2 65. Asp was only detected weakly in positive ion mode and consequently negative ion mode was used with the same LC conditions. L-Asp eluted at $t_R$ 6.1 min, indicating that the configuration of the Asn unit was L. The retention times ($t_R$, min; MRM ion pair, parent→product) of the authentic standards were as follows: L-Asp (6.1; 132→88), D-Asp (6.8). The MS parameters used were as follows: DP −30.0, EP −5.0, CE −18.5, CXP −13.0, CUR 30, CAD High, IS −4500, TEM 750, GS1 65, GS2 65.

A sample of compound 3 was treated with 6 N HCl at 110° C. for 24 h. The hydrolysate was concentrated to dryness, reconstituted in 100 µL H$_2$O and then analyzed by chiral HPLC [column, Chirobiotic TAG (4.6×250 mm), Supelco; solvent, MeOH-10 mM NH$_4$OAc (40:60, pH 5.33): flow rate, 0.5 mL/min; detection by ESIMS in positive ion mode (MRM scan)]. N-Me-L-Glu, L-Ile, L-Leu, L-Pro and N-Me-D-Phe eluted at $t_R$ 6.0, 8.3, 8.6, 13.3 and 41.7 min, respectively. The retention times ($t_R$, min; MRM ion pair, parent→product) of the authentic standards were as follows: N-Me-L-Glu (6.0; 162-44), N-Me-D-Glu (15.8), L-Ile (8.3; 132→86), L-allo-Ile (8.5), D-allo-Ile (19.6), D-Ile (22.2), L-Leu (8.6; 132→86), D-Leu (19.8), L-Pro (13.3; 116→70), D-Pro (35.2), N-Me-L-Phe (23.2; 180→134), and N-Me-D-Phe (41.7). To further separate the isobaric Ile and Leu units, different LC conditions were employed [column, Chirobiotic TAG (4.6× 250 mm), Supelco; solvent, MeOH-10 mM NH$_4$OAc (90:10, pH 5.65); flow rate, 0.5 mL/min; detection by MS (MRM scan)]. L-Ile and L-Leu eluted at $t_R$ 12.3 and 13.1 min, respectively. The retention times ($t_R$, min; MRM ion pair, parent→product) of the authentic amino acid standards were as follows: L-Ile (12.3; 132→86), L-allo-Ile (13.4), D-allo-Ile (57.5), D-Ile (70.5), L-Leu (13.1; 132→86), and D-Leu (51.7). The MS parameters used were as follows: DP 31.0, EP 8.0, CE 17.3, CXP 3.1, CUR 35, CAD Medium, IS 4500, TEM 750, GS1 65, GS2 65.

Hmpa in the hydrolysate of compound 3 was detected in negative ion mode [column, Chirobiotic TAG (4.6×250 mm), Supelco; solvent, MeOH-10 mM NH$_4$OAc (40:60, pH 5.35); flow rate, 0.5 mL/min; detection by ESIMS in negative ion mode (MRM scan)]. The MS parameters used were as follows: DP −35.0, EP −8.0, CE −17.9, CXP −1.7, CUR 40, CAD Medium, IS −4500, TEM 750, GS1 65, GS2 65. (2R, 3S)-Hmpa from the hydrolysate eluted at $t_R$ 6.4 min. The retention times ($t_R$, min; MRM ion pair, parent→product) of the authentic standards were as follows: (2S,3R)-Hmpa (6.0; 131→85), (2S,3S)-Hmpa (6.2; 131→85), (2R,3S)-Hmpa (6.4; 131→85), (2R,3R)-Hmpa (7.0; 131→85). The hydrolysate was examined under different HPLC conditions in order to confirm this assignment [column, Chiralpak MA (+) (4.6× 50 mm), Daicel Chemical Industries, Ltd.; solvent, 2 mM CuSO$_4$—CH$_3$CN (85:15); flow rate, 1.0 mL/min; detection by UV absorption at 254 nm]. (2R,3S)-Hmpa from the hydrolysate eluted at $t_R$ 15.4 min. The retention times ($t_R$, min) of the authentic standards were as follows: (2R,3S)-Hmpa (15.4), (2R,3R)-Hmpa (17.9), (2S,3R)-Hmpa (22.7), (2S,3S)-Hmpa (27.5). Under these conditions, all other units eluted at $t_R$<6.5 min.

Example 3

Base Hydrolysis to Determine Configuration of HIVA Units

The acid hydrolysate of compound 1 was analyzed by chiral HPLC [column, Chirobiotic TAG (4.6×250 mm), Supelco; solvent, MeOH-10 mM NH$_4$OAc (60:40, pH 5.63); flow rate, 0.5 mL/min; detection by ESIMS in negative ion mode (MRM scan)]. Both L-Hiva and D-Hiva were detected at $t_R$ 6.0 and 6.4 min, respectively. The retention times ($t_R$, min; MRM ion pair, parent→product) of the authentic standards were as follows: L-Hiva (6.0; 117→71), D-Hiva (6.4). A sample of compound 1 (100 µg) was suspended in 80 µL MeOH-0.5 N NaOH (1:1) and left to stand at room temperature for 72 h. The solution was neutralized by the addition of 20 µL 1 N HCl, and was then analyzed by chiral HPLC-MS.

Only L-Hiva was detected at $t_R$ 6.0 min. The retention times ($t_R$, min; MRM ion pair, parent→product) of the authentic standards were as follows: L-Hiva (6.0; 117→71), D-Hiva (6.4). The MS parameters used were as follows: DP −30.0, EP −3.0, CE −17.3, CXP −2.0, CUR 45, CAD Medium, IS −4500, TEM 650, GS1 50, GS2 25.

Example 4

Modified Marfey's Analysis to Determine Configuration of Statine Units

Samples of both compounds 1 and 3 (35 µg) were subjected to acid hydrolysis, derivatized with L-FDLA, and analyzed by reversed-phase HPLC [column, Alltima HP C18 HL (4.6× 250 mm), 5 µm, Alltech; flow rate, 0.5 mL/min; detection by ESIMS in negative ion mode (MRM scan, 468→408)], using a linear gradient of MeOH in H$_2$O (both containing 0.1% HCOOH, 40-100% MeOH over 50 min). Two peaks, corresponding to (3S,4S)-Sta-L-FDLA and (3R,4S)-Sta-L-FDLA, were observed in both samples in a 1:1 ratio at $t_R$ 35.5 and 35.9 min, respectively. The retention times ($t_R$, min) of the authentic standards were as follows: (3S,4S)-Sta-L-FDLA (35.5), (3R,4S)-Sta-L-FDLA (35.9), (3S,4S)-Sta-D-FDLA [corresponding to (3R,4R)-Sta-L-FDLA, 45.7], (3R,4S)-Sta-D-FDLA [corresponding to (3S,4R)-Sta-L-FDLA, 46.4]. The MS parameters used were as follows: DP −60.0, EP −7.0, CE −28.0, CXP −7.4, CUR 40, CAD High, IS −4500, TEM 750, GS1 40, GS2 40.

Example 5

Structure Analysis and Determination

HRESI/APCIMS and NMR data for compound 1 suggested a molecular formula of C$_{58}$H$_{95}$N$_9$O$_{16}$ (m/z 1196.6812 for [M+Na]$^+$, 1174.6988 for [M+H]$^+$, 598.8455 for [M+H+Na]$^{2+}$, and 587.8544 for [M+2H]$^{2+}$). Perusal of the $^1$H and $^{13}$C NMR spectra revealed that it was a depsipeptide (FIG. 1), with several exchangeable proton signals characteristic of amides ($\delta_H$~6 to ~8), α-protons ($\delta_H$~4 to ~5), and some deshielded signals in both the $^1$H and $^{13}$C NMR spectra indicative of methines adjacent to an ester linkage ($\delta_{H/C}$ 5.13/ 78.1 and 4.70/77.5). There were also several N-methyl signals ($\delta_H$ 3.01 and 2.30) and one O-methyl apparent ($\delta_H$ 3.72). In addition two conformers were present in the ratio 15:1. It is believed that the minor signals present in the CDCl$_3$ NMR spectra were due to conformers and not impurities, as these were not observed in the spectra obtained in DMSO-d$_6$.

Analysis of the $^1$H NMR, $^{13}$C NMR, APT, COSY, edited HSQC, HMBC, ROESY and TOCSY spectra in CDCl$_3$ of compound 1 (FIG. 1) revealed the presence of four regular amino acid units (Ala, Thr, Asn and Leu) and two hydroxy-isovaleric acid (Hiva) moieties. In addition, O-Me-Pro, N-Me-Phe, N,N-Me$_2$-Val and statine (Sta, C-25-C-32) were deduced. Given that there were two terminal groups (O-Me-Pro and N,N-Me$_2$-Val), it was clear from the degree of unsaturation that the compound was linear (all 16 double bond equivalents were accounted for). The hydroxyl protons for Sta and Thr units were evident and thus precluded branching of the chain through ester linkages at these positions (note: the threonine hydroxyl was observed only in the NMR spectra collected in DMSO-d$_6$). The fragments Sta-Thr-Ala-N-Me-Phe-O-Me-Pro and N,N-Me$_2$-Val-Hiva-Hiva-Leu-Asn were readily constructed with the help of HMBC and ROESY data. The continuous sequence of the two fragments was confirmed by ESIMS fragmentation (FIG. 5). Without other evidence, however, it was still unclear whether the Sta and Asn units were joined through C-1 or C-4 of Asn (C-33 and C-36 in compound 1), as no correlations were observed through the NH$_2$ group or from the NH or H-28 in the Sta unit. Collection of NMR data for compound 1 in DMSO-d$_6$ revealed an extra HMBC correlation from one of the NH$_2$ amide protons to the β-carbon of Asn, thus determining the chain proceeded through C-1.

A portion of compound 1 was hydrolysed (6 N HCl, 110° C., 24 h) and analyzed by chiral HPLC-MS. This revealed the presence of L-Pro, N-Me-D-Phe, L-Ala, L-Thr, L-Asp, L-Leu and N,N-Me$_2$-L-Val. The presence of L-Asp in the hydrolysate is consistent with the presence of L-Asn in the intact molecule, the primary amide having undergone hydrolysis. In addition, peaks corresponding to both L- and D-Hiva were detected, indicating two units of opposite configuration were present. To assign their order, another portion of compound 1 was subjected to base hydrolysis (0.5 N NaOH/MeOH 1:1, rt, 72 h) to selectively hydrolyze the ester bonds and liberate the two terminal units (Hiva-2 and N,N-Me$_2$-Val). Chiral analysis of the base hydrolysate indicated the presence of L-Hiva only, thus determining the configuration shown for compound 1.

To establish the configuration of the Sta, a portion of the acid hydrolysate of compound 1 was derivatized with L-FDLA and subjected to modified Marfey's analysis (see Marfey et al. *Carlsburg Res. Commun.* 1984, 49, 591-596). Peaks corresponding to both (3S,4S)- and (3R,4S)-Sta-L-FDLA were detected, probably due to epimerization at C-3 resulting from dehydration/rehydration. An attempt to confirm the relative configuration of this unit in situ by J-based analysis failed (Matsumori et al. *J. Org. Chem.* 1999, 64, 866-876), probably because the small H-27-H-28 coupling (2.7 Hz) precluded measurement of heteronuclear coupling constants by HETLOC across this bond (see, e.g., Luesch et al., *J. Am. Chem. Soc.* 2001, 123, 5418-5423; and Uhrin et al., *J. Magn. Reson.* 1998, 130, 155-161). It was recently shown that the relative configuration of statine and statine-like units derived from other amino acids can be easily determined by examination of the coupling constants of the α-methylene signals (Preciado, A. et al., *J. Org. Chem.* 2008, 73, 9228-9234). The downfield H-2a signal (H-26a) shows a large coupling to H-27 and the upfield H-26 (H-26b) shows a small coupling to H-27 (8.7 and 5.4 Hz, respectively), thus indicating that the configuration is 3S,4S.

HRESI/APCIMS of compound 2 suggested a molecular formula of C$_{59}$H$_{97}$N$_9$O$_{16}$ (m/z 1226.6687 for [M+K]$^+$, 1210.6936 for [M+Na]$^+$, and 1188.7119 for [M+H+Na]$^{2+}$), and the $^1$H NMR spectrum indicated a striking similarity to compound 1, including the same conformational ratio. Examination of the $^1$H NMR, COSY, HMQC, HMBC, ROESY and TOCSY spectra of compound 2 (FIG. 1) revealed the presence of the same units found in compound 1, except for 2-amino-butyric acid (Aba) in place of Ala. The close similarity of proton and carbon chemical shifts between compounds 1 and 2 indicated that compound 2 had the same sequence and relative configuration as compound 1. Compounds 1 and 2 exhibited very similar optical rotation ([α]$^{20}_D$ −4.4 and −5.0 respectively), indicating that they have the same absolute configuration. The sequence of compound 2 was confirmed by ESIMS fragmentation (FIG. 5).

The m/z peak at 1009.5941, for [M+Na], in the HRESI/APCIMS and NMR data for compound 3 suggested a molecular formula of C$_{50}$H$_{82}$N$_8$O$_{12}$. Analysis of the $^1$H NMR spectrum suggested that the compound was a peptide (amide signals at $\delta_H$ 6-8, α-proton signals at $\delta_H$ ~4-5.5) with at least two conformers, the most prominent of which exists in the ratio of 2.45:1. Aromatic signals ($\delta_H$ 7.2-7.3), putative N-methyl singlets ($\delta_H$ 3.090, 3.087, 3.05 and 2.77) and an O-methyl singlet ($\delta_H$ 3.75) were also observed. Analysis of the $^1$H NMR, COSY, edited HSQC, HMBC, ROESY and TOCSY spectra of compound 3 recorded in CDCl$_3$ revealed the presence of four regular α-amino acids (Pro, Gly, Be, Leu), two N-methylated α-amino acids (N-Me-Phe, N-Me-Gln), one hydroxy acid (2-hydroxy-3-methylpentanoic acid, Hmpa), and Sta (C-25-C-32, FIG. 2). The sequence N-Me-Phe-Gly-Ile-Sta-Gln-Leu-Hmpa could be determined by HMBC analysis. A ROESY correlation between H-5a and H-8 allowed the joining of O-Me-Pro to N-Me-Phe. ROESY data also confirmed the HMBC sequence (FIG. 2). It was unambiguously established that C-5 of N-Me-Gln (C-37 in compound 3) was the primary amide carbon, by virtue of the HMBC correlation of H-28 to C-33 and correlations from H-34 and H$_3$-38 to C-39. Additionally, there was a [M−128]$^+$ peak at m/z 858.5322 in the HRESI/APCIMS which was consistent with loss of O-Me-Pro (calcd for C$_{44}$H$_{72}$N$_7$O$_{10}$, 858.5341). By default, an OH group was proposed at C-46, and this was supported by the proton chemical shift at this position ($\delta_H$ 4.15), which suggested OH rather than an acyloxy group. The sequence was further confirmed by ESIMS fragmentation (FIG. 6).

A portion of compound 3 was hydrolysed (6 N HCl, 110° C., 24 h) and analyzed by chiral HPLC-MS. Peaks corresponding to L-Pro, N-Me-D-Phe, L-Ile, N-Me-L-Glu, and L-Leu were detected. The presence of N-Me-L-Glu in the hydrolysate is consistent with the presence of N-Me-L-Gln in the intact molecule, as the primary amide have undergone hydrolysis. The four stereoisomers of Hmpa eluted very closely together, but a putative assignment of (2R,3S)-Hmpa was made. This was later confirmed by analysis of the hydrolysate by conventional chiral HPLC with a different column, under conditions where the four stereoisomers eluted further apart (see assays described herein). A portion of the hydrolysate was then derivatized with L-FDLA as with compound 1, and once again, two peaks were detected corresponding to (3R,4S)-Sta-L-FDLA and (3S,4S)-Sta-L-FDLA. The further downfield of the CH$_2$ protons at C-26 showed a large coupling constant to H-27 (9.3 Hz), indicating that the configuration of this unit is 3S,4S (see Preciado et al., *J. Org. Chem.* 2008, 73, 9228-9234).

The data for each of grassystatins A (compound 1), B (compound 2) and C (compound 3) is summarized as follows:

Grassystatin A (1):

Colorless amorphous solid; $[\alpha]^{20}_D$ −4.4 (c 0.08, MeOH); UV (MeOH) $\lambda_{max}$ (log ε) 206 (4.93), 258 (4.03), 324 (3.2); IR (film) $v_{max}$ 3291 (br), 3068 (w), 3054 (w), 3019 (w), 2955, 2937, 2925, 2914, 2851, 2360, 2342, 1733, 1646, 1540, 1457, 1374 (w), 1265, 1109 (w), 1023 (w), 896 (w), 739; NMR data, $^1$H NMR, $^{13}$C NMR, APT, COSY, HMQC, HMBC, ROESY, TOCSY in CDCl$_3$, see Table 1, $^1$H NMR, COSY, edited HSQC, HMBC, ROESY in DMSO-d$_6$; HRESI/APCIMS m/z [M+Na] 1196.6812 (calcd for $C_{58}H_{95}N_9O_{16}Na$, 1196.6794), [M+H]$^+$ 1174.6988 (calcd for $C_{58}H_{96}N_9O_{16}$ 1174.6975), [M+H+Na]$^{2+}$ 598.8455 (calcd for $C_{58}H_{96}N_9O_{16}Na$, 598.8436), [M+2H]$^{2+}$ 587.8544 (calcd for $C_{58}H_{97}N_9O_{16}$, 587.8527).

Grassystatin B (2):

Colorless amorphous solid; $[\alpha]^{20}_D$ −5.0 (c 0.1, MeOH); UV (MeOH) $\lambda_{max}$ (log ε) 202 (4.47), 266 (2.96), 320 (2.45); IR (film) $v_{max}$ 3276 (br), 3079 (w), 3054 (w), 3017 (w), 2961, 2927, 2874, 2360, 2342, 1752, 1732, 1690, 1627, 1549, 1493 (w), 1463 (w), 1436 (w), 1389 (w), 1369 (w), 1267 (w), 1207 (w), 1179 (w), 1124 (w), 1023 (w); NMR data, $^1$H NMR, COSY, HMQC, HMBC, ROESY, TOCSY in CDCl$_3$, see Table 1; HRESI/APCIMS m/z [M+K]$^+$ 1226.6687 (calcd for $C_{59}H_{97}N_9O_{16}K$, 1226.6690), [M+Na] 1210.6936 (calcd for $C_{59}H_{97}N_9O_{16}Na$, 1210.6951), [M+H]$^+$ 1188.7119 (calcd for $C_{59}H_{98}N_9O_{16}$, 1188.7131), [M+H+Na]$^{2+}$ 605.8516 (calcd for $C_{59}H_{98}N_9O_{16}Na$, 605.8515).

Grassystatin C (3):

Colorless amorphous solid; $[\alpha]^{20}_D$ −21.9 (c 0.04, MeOH); UV (MeOH) $\lambda_{max}$ (log ε) 203 (4.74), 260 (2.89), 320 (2.17); IR (film) $v_{max}$ 3307 (br), 3078 (w), 3054 (w), 3016 (w), 2659, 2927, 2904, 2874, 2361, 2340, 1742, 1635, 1531, 1462, 1442, 1410, 1368, 1285 (w), 1199 (w), 1047 (w); NMR data, $^1$H NMR, COSY, edited HSQC, HMBC, ROESY, TOCSY in CDCl$_3$, see Table 2; HRESI/APCIMS m/z [M+Na] 1009.5941 (calcd for $C_{50}H_{82}N_8O_{12}Na$, 1009.5950), [M−128]$^+$ 858.5322 (calcd for $C_{44}H_{72}N_7O_{10}$, 858.5341).

It was found that grassystatins A-C (1-3) structurally varied from cyanobacterial metabolites tasiamide B and tasiamide (see FIG. 4).

Example 6

Protease Inhibition Screen

Compound 1 was added into the reaction buffer containing enzyme by acoustic droplet ejection (Echo 550, Labcyte Inc., Sunnyvale, Calif.) such that the final concentration was 10 µM. After incubation at room temperature for 10-15 min, the substrate was added, after which fluorescence at each relevant Ex/Em wavelength was measured every 5 min for 2 h. The substrate alone in the reaction buffer served as background. The activity of compound 1 was evaluated by obtaining % enzyme activity relative to the slope of no inhibitor control. Each enzyme assay was performed in duplicate by Reaction Biology Corp. (Malvern, Pa.).

Example 7

Protease Inhibition Assays

Assays for compounds 1 and 2 were carried out in the same way as in the protease screen, using 3-fold serial dilutions in DMSO, starting at 10 µM and 100 µM respectively, with 10 different concentrations of each. Compound 3 was insoluble in DMSO, and thus a dilution series in EtOH was used. For compounds 1-3, a 3-fold dilution series starting at 100 µM was used, with 10 different concentrations. Assays were carried out by Reaction Biology Corp. (Malvern, Pa.). Enzyme activity (in %), calculated as above, was used to determine $IC_{50}$ values with non-linear regression in GraphPad Prism (GraphPad Software, Inc., La Jolla, Calif.).

Three metalloproteases in the ADAM family were identified in the primary screen of compound 1 (ADAMS, ADAM10 and TACE). Only one of the hits (TACE), however, could be replicated in a dose-response assay (FIG. 3). Inhibition of TACE by compounds 1-3 was concentration- and time-dependent (FIG. 8B), with $IC_{50}$s of 1.23, 2.23 and 28.6 µM, respectively.

Example 8

Cellular Uptake and Inhibition of Cellular Cathepsins

The cellular uptake of grassystatin A (1) was measured as described previously in MCF7 cells (see Zaidi, N. et al., Biochem. Biophys. Res. Commun. 2007, 364, 243-249). MCF7 cells were cultured in Dulbecco's Modified Eagle Medium (DMEM, Invitrogen) containing 10% fetal bovine serum (FBS, HyClone, Logan, Utah), in a humidified atmosphere containing 5% $CO_2$ at 37° C. Briefly, MCF7 cells were seeded into 24-well plates. When cells reached 80-100% confluency, compound 1 or pepstatin A was added. After 1 h incubation the medium was removed and the cells were trypsinized for 10 min, before being collected by centrifugation and lysed with NP-40 lysis buffer (1% NP-40, 50 mM NaOAc, pH 4.0). The lysate (50 µL) from each well was incubated at 37° C. with 10 µM Mca-Gly-Lys-Pro-Ile-Leu-Phe-Phe-Arg-Leu-Lys(Dnp)-D-Arg-NH$_2$ (the same substrate used for cathepsin D and E in other assays) in 50 mM NaOAc (pH 4.0, total volume 100 µL). The reaction was monitored by measuring the increase in fluorescence ($\lambda_{ex}$=320 nm, $\lambda_{em}$=405 nm).

To measure the in vitro inhibition of cellular cathepsins by compound 1 and pepstatin A, kinetic assays were carried out in the same manner, using lysate prepared from untreated MCF7 cells. The test compounds were added to a mixture of the reaction buffer and the substrate (50 µL). The reaction was initiated by the addition of 50 µL cell lysate, and then monitored in the same way.

FIGS. 9(A-B) present inhibitory activities of grassystatin A (1) and pepstatin A against MCF7 cellular proteases as determined with a cathepsin D/E substrate. FIG. 9A shows activities of MCF7 cells treated with grassystatin A (1) or pepstatin A. Cells were lysed and the protease activity of the lysates assessed. FIG. 9B relates to MCF7 cell lysate directly treated with grassystatin A (1) or pepstatin A (*Denotes significance of P<0.05 using a two-tailed t test. Data points are shown±SD). Notably, the selectivity between cathepsins D and E by grassystatin A (1) was greater than pepstatin A.

Example 9

Isolation of PBMC and Culture of Monocytes and DC

PBMCs were isolated from buffy coats (leukopac, PBL) obtained from Lifesouth Community Blood Center (Gainesville, Fla., USA) by Ficoll-Hypaque density gradient centrifugation using Lymphoprep (Axis-Shield, Norway). Briefly, the contents of the buffy coat were diluted to three times its volume in sterile 1×PBS pH 7.4 (Gibco, California, USA). The dilution was layered onto the Lymphoprep in a 2:1 ratio. The sample was then centrifuged for 25 min at room temperature and 250 g. The PBMCs were collected at the interface, washed twice with PBS and centrifuged each time for 10 min at 4° C. and 250 g. Cell viability was assessed by trypan blue exclusion. All cultures of human PBMC and derived cells were maintained in RPMI 1640 medium (Sigma, Missouri, USA) supplemented with 2 mM L-glutamine (Life Technologies, Paisley, Scotland), 5000 U/mL penicillin (Sigma, Missouri, USA), 5000 U/mL streptomycin sulfate (Sigma, Missouri, USA), and 10% v/v fetal bovine serum (Gibco, California, USA). PBMCs were either used in an experiment with compound 1 at various concentrations or separated further.

Monocytes were obtained by adhering $5 \times 10^6$ PBMCs/mL to a flask for 2 h at 37° C. After removing the supernatant containing non-adherent cells, adherent monocytes were washed with 1×PBS pH 7.4. Complete media was added to the remaining cells. To induce differentiation into DCs 50 ng/mL GM-CSF (Leukine, Berlex, Wash., USA) and 20 ng/mL IL-4 (BD Biosciences) were added to the culture for 7 days.

Example 10

Isolation of CD4+ T Helper Cells from PBMCs

CD4+ T cells were purified from PBMCs by negative-selection using the "Human CD4+ T Cell Enrichment" kit (EasySep, StemCell Technologies, Vancouver, BC, Canada) by following the manufacturer's protocol. Briefly, cells were resuspended in magnesium-free 1×PBS with 2% fetal bovine serum in 12×75 mm polystyrene tubes at $5 \times 10^7$ cells/mL. 50 μL/mL of enrichment cocktail was added, incubated for 10 min at room temperature and then followed by 100 μL/mL nanoparticle cocktail and extra incubation. Afterwards the total volume was brought to 2.5 mL and the tube was put into an EasySep magnet. After 5 min incubation to allow for magnetic beads to attach to the side of the tube, the contents were decanted into a clean tube. The beads were washed once more to increase cell purity. Cells were subsequently used in Mixed Lymphocyte Reactions (MLRs).

Example 11

Mixed Lymphocyte Reactions (MLRs)

Autologous or allogeneic enriched CD4+ T cells were labeled for 15 min with 200 nM carboxyfluorescein diacetate, succinimidyl ester (CFSE, Molecular Probes, Eugene Oreg.) according to manufacturer's protocol and cultured at $1 \times 10^6$ cells/mL. Monocyte-derived DCs (MoDC), pulsed with 5 μg/mL Tetanus Toxin C-fragment (TTc, Roche Diagnostics, Mannheim, Germany) and phorbol 12-myristate 13-acetate (PMA, Promega, Madison, Wis.), were added to the same culture at a ratio of 1:2 in combination with increasing concentrations of compound 1. The cell mixture was allowed to incubate for 5 days in a water-jacketed incubator at 37° C. Afterwards, culture cells were collected for flow-cytometric analysis.

It was found that compound 1 was able to reduce antigen-stimulated T cell proliferation in PBMCs (FIG. 10A) and antigen presentation by DCs to $T_H$ cells (FIG. 10B). The experiments using pepstatin A were previously reported (see Zaidi et al., *Biochem. Biophys. Res. Commun.* 2007, 364, 243-249; Burster et al., *Biochem. Biophys. Res. Commun.* 2008, 377, 1299-1303; Chain et al., *J. Immunol.* 2005, 174, 1791-1800; and Zhang et al. *Biochem. Biophys. Res. Commun.* 2000, 276, 693-701). FIG. 10A shows that downregulation of the activation of CD3+ T cells on whole PBMC after treatment with different concentrations of compound 1. FIG. 10B shows downregulation of $T_H$ activation (proliferation) by the addition of different concentrations of compound 1 ("Ctrl" refers to T cells that did not have DCs added to them. *Denotes significance of P<0.05 using a two-tailed t test. Data points are shown±SEM).

Example 12

Flow Cytometry

IFN-γ is a pro-inflammatory molecule and the signature cytokine produced by $T_H1$ cells that, among other effects, activates macrophages (Janeway et al., T cell-mediated immunity. In *Immunobiology, The Immune System in Health and Disease*, 5th ed.; Garland Publishing: New York, 2001; 295-340). These cells are strongly involved in cellular immunity against cancer and intracellular pathogens such as viruses, but are also involved in the etiology of transplant rejection (Dunn et al., *Immunol. Res.* 2005, 32, 231-245). IL-17 is another pro-inflammatory cytokine, produced by a recently described subset of T cells, $T_H17$ cells (see Tesmer et al., *Immunol. Rev.* 2008, 223, 87-113).

$T_H17$ cells and IL-17 have been implicated in a number of autoimmune and allergic diseases such as rheumatoid arthritis and asthma (see Tesmer et al., *Immunol. Rev.* 2008, 223, 87-113). Because of their involvement in proinflammatory disorders and the association of such pathologies with the activation of T cells by antigen presentation, the contribution of compound 1 to the modulation or downregulation of pro-inflammatory cytokines was investigated.

Experimental pelleted cells were incubated for 30 min at 4° C. with antibodies and washed with staining buffer (PBS+2% BSA+0.1% Na azide). Subsequently intracellular staining was carried out by first adding Cytofix/Cytoperm to increase the permeability of cells followed by another round of staining before fixing with 2% paraformaldehyde. Quantitation was carried out using FCS Express (version 3, De Novo Software, Los Angeles, Calif.) by gating for lymphocytes based on forward and side scatter properties followed by analysis of the percentages of positively stained quadrants. 50,000 cells were analyzed for each sample and isotype-specific immunoglobulin controls were run for each fluorochrome. Stains used in PBMC experiments were CD3-APC, CFSE and 7-AAD (eBioscience); those used in CD4+ T cells for MLRs were CFSE, 7-AAD, AlexaFluo 647-conjugated anti-IL-17 and PE-conjugated anti-IFN-γ (BD Biosciences).

It was found that compound 1 reduced production of interleukin-17 (IL-17) (FIG. 10C) and interferon-γ (IFN-γ) (FIG. 10D) by T cells. FIGS. 10C and D demonstrate effects of compound 1 on the production of intracellular IFNγ (FIG. 10C) and IL-17 (FIG. 10D) by $T_H$ cells induced by autologous activated DC ("Ctrl" refers to T cells that did not have DCs added to them. *Denotes significance of P<0.05 using a two-tailed t test. Data points are shown±SEM).

Example 13

Protease Profiling and Cellular Activity

A slow onset of inhibition indicates slow binding of the inhibitor, and is apparent by a noticeable curve in the progress curve of the reaction within a timescale where the uninhibited reaction is still linear (Copeland et al., Wiley & Sons: Hoboken, 2005, 141-177). Statine-based slow-binding inhibitors of aspartic proteases have been described (Marcinkeviciene et al. *J. Biol. Chem.* 2001, 276, 23790-23794). There are several examples of slow-binding inhibitors of zinc metalloproteases and slow-binding inhibitors of MMPs (see Bull et al., *J. Biol. Chem.* 1985, 260, 2952-2962; and Bernardo et al., *J. Biol. Chem.* 2002, 277, 11201-11207). The reason for slow-binding may be the expulsion of a tightly bound, catalytically active water molecule from the active site (Copeland et al., In *Evaluation of Enzyme Inhibitors In Drug Discovery: A Guide for Medicinal Chemists and Pharmacologists*, Wiley & Sons: Hoboken, 2005; pp 141-177). With slow binding inhibitors, the onset of inhibition depends on the preincubation time of the test compound with the enzyme.

To test activity and to probe selectivity for certain aspartic and other proteases, compound 1 were tested against a panel of proteases to identify inhibitory activity at 10 μM. Compound 1 was found to be active against a subset of aspartic proteases—cathepsin D and cathepsin E. The other proteases with compromised activities were the metalloproteases ADAMS, ADAM10 and TACE. Subsequent validation of these hits revealed that the greatest activity compound 1 was against cathepsin E.

FIG. 7 presents the results of protease screen treated with grassystatin A (1) (10 μM). The values as shown represent % enzyme activity compared to solvent control, and additionally represented in a continuous color scale.

Further, test results show that compounds 1-3 all showed selectivity for cathepsin E over cathepsin D compared to pepstatin A. In particular, compound 1 selectively inhibited cathepsin D and cathepsin E with $IC_{50}$s of 26.5 nM and 886 pm respectively. And compound 2 selectively inhibited cathepsin D and cathepsin E with $IC_{50}$s of 7.27 nM and 354 pm respectively, while pepstatin A inhibited cathepsin D and cathepsin E with $IC_{50}$s of 173 pm and 181 pm respectively. The results show that compounds 1-3 inhibited cathepsin D and E, and they were selective for cathepsin E (~20 to ~30 fold), while pepstatin A did not discriminate between these proteases.

Notably, compounds 1-3 discriminate between these two enzymes, while pepstatin A does not. It was demonstrated the inhibition of cathepsins in a cellular system, and also the disruption of antigen presentation by dendritic cells (DCs), a process in which cathepsin E has been implicated (Zaidi et al., *Biochem. Biophys. Res. Commun.* 2008, 377, 327-330; and Zaidi et al. *Biochem. Biophys. Res. Commun.* 2008, 367, 517-522). Compound 1 may be used as a valuable probe for the study of cathepsin E function, as it was selective against cathepsin E.

Of the metalloproteases, only TACE inhibition was validated in the second round of assays (FIG. 3). $IC_{50}$s against ADAM9 and ADAM10 were in the high micromolar range or above 100 μM. The $IC_{50}$s of TACE inhibition were in the low micromolar range, and, in contrast to the dose-dependent but time-independent inhibition of cathepsins (FIG. 8A), analysis of the progress curves revealed concentration- and time-dependent inhibition (FIG. 8B). In the large scale screen, this time may have been longer than desirable, leading to an apparent lower $IC_{50}$ for compound 1 against ADAM9 and ADAM10.

To assess whether grassystatin A (compound 1) is able to enter cells and inhibit target enzymes in a cellular context, MCF7 cells were treated for 1 h with various concentrations of compound 1. After this time, cells were washed, lysed and then the protease activity of the lysate was measured with a fluorogenic cathepsin D/E substrate (see FIG. 9A). For comparison, cells were also treated with the same concentrations of pepstatin A (FIG. 9A), and the in vitro inhibition of cellular enzymes was measured by adding compounds directly to cell lysate (FIG. 9B). The apparent $IC_{50}$s of compound 1 and pepstatin A in a cellular system were fairly similar (FIG. 9A). However, the apparent in vitro $IC_{50}$ of compound 1 against MCF7 lysate was ~0.5 μM, and that of pepstatin A was ~5 nM. This discrepancy likely reflects these compounds' differing specificity towards cathepsins D and E—compound 1 is able to inhibit a smaller fraction of the enzymes (predominantly cathepsin E) that cleave the substrate compared to pepstatin A. Taken together, the results suggest that compound 1 is able to more efficiently enter cells than pepstatin A, which is known to have poor cell permeability (see Zaidi et al., *Biochem. Biophys. Res. Commun.* 2007, 364, 243-249).

Example 14

Investigation of Effects of the Compounds on Antigen Presentation

Cathepsin E is thought to have a functional role in the proteolysis of antigenic peptides, which are subsequently presented as antigens on the surface of antigen presenting cells (APCs) in the major histocompatability complex (MHC) class II pathway (see, e.g, Zaidi et al., *Biochem. Biophys. Res. Commun.* 2007, 364, 243-249; Burster et al., *Biochem. Biophys. Res. Commun.* 2008, 377, 1299-1303; Nishioku, T. et al., *J. Biol. Chem.* 2002, 277, 4816-4822; and Chain et al., *J. Immunol.* 2005, 174, 1791-1800; and Zhang, T. et al., *Biochem. Biophys. Res. Commun.* 2000, 276, 693-701).

Exogenous antigens are internalized by APCs and proteolytically cleaved within endosomes, before they are presented on the cell surface bound to MHC class II proteins (Janeway et al., T cell-mediated immunity. In *Immunobiology, The Immune System in Health and Disease*, 5$^{th}$ ed.; Garland Publishing: New York, 2001; 295-340). The invariant chain (Ii) is a chaperone that prevents endogenous peptides from binding to MHC class II proteins while they are transported from the endoplasmic reticulum to endosomes (Janeway et al., In *Immunobiology, The Immune System in Health and Disease*, 5$^{th}$ ed.; Garland Publishing: New York, 2001, 155-184) Ii undergoes several cleavage steps both before and after entering the endosome. Its removal allows antigens to bind MHC II for subsequent presentation. The role of cysteine proteases in Ii cleavage has been reported (Riese et al., *J. Clin. Invest.* 1998, 101, 2351-2363; Marić et al. *Proc. Natl. Acad. Sci. USA* 1994, 91, 2171-2175; Zhang et al. *Biochem. Biophys. Res. Commun.* 2000, 276, 693-701; Nishioku et al., *J. Biol. Chem.* 2002, 277, 4816-4822; and Chain et al. *J. Immunol.* 2005, 174, 1791-1800). Further, Costantino et al. (*J. Immunol.* 2008, 180, 2876-2885) presented results suggesting that the role of different enzymes in Ii cleavage is highly variable and there is a large degree of redundancy.

Antigen presentation to T cells stimulates their proliferation and the release of certain inflammatory cytokines (vide infra) (see Janeway et al., In *Immunobiology, The Immune System in Health and Disease*, 5$^{th}$ ed.; Garland Publishing: New York, 2001, pp 295-340). The effect of compound 1 on human peripheral blood mononuclear cells (PBMCs) was investigated. PBMCs are a mixture containing various APCs (dendritic cells, B cells and macrophages) and T cells. The effect of compound 1 on T cells was examined using flow cytometry to gate for CD3$^+$ lymphocytes (T cells).

It was found that 10 μM of compound 1 was able to significantly reduce T cell proliferation in response to exogenous antigen (Tetanus toxin C-fragment, TTc, FIG. 10A). In the same experiment, T cell viability was unaffected (data not shown).

The effect of compound 1 on the interaction between monocyte derived dendritic cells (DCs) and CD4+ T cells (T helper cells, $T_H$) was then investigated, in a mixed lymphocyte reaction (MLR). The first experiments were autologous MLRs, where DCs and T cells came from the same human donor. DCs were chosen for this study as they are the most potent antigen presenting cells and have much higher cathepsin E expression than other APCs (see Zaidi, N. et al., *FEBS J.* 2007, 274, 3138-3149) The main targets of antigen presentation are $T_H$ cells, which go on to orchestrate the ensuing immune response. An enriched population of these cells as the responders were then used in the assay. Differentiated DCs were cultured in the presence of antigen (TTc), phorbol 12-myristate 13-acetate (PMA) and $T_H$ cells for 5 days.

Compound 1 was able to reduce T cell proliferation in a dose dependent manner (FIG. 10B). TTc and PMA alone (i.e., in the absence of DCs) were unable to increase T cell proliferation, and thus this effect of compound 1 is dependent on DCs. In the experiments, it was found that compound 1 was able to inhibit upregulation of interleukin-17 (IL-17) (FIG. 10C) and interferon-γ (IFN-γ) (FIG. 10D) in response to antigen presentation.

To determine whether compound 1 had any effect on T cell recognition of foreign MHC II proteins, the same experiment with DCs and $T_H$ cells from different donors was performed. It was found that compound 1 had no effect on DC stimulated proliferation in an allogeneic MLR. This is likely because T cells were recognizing non-self MHC II proteins on the surface of DCs (see Janeway et al., In *Immunobiology, The Immune System in Health and Disease*, Garland Publishing: New York, 2001).

Further, even though proliferation was not reduced, a significant downregulation of IL-17 and IFN-γ production was observed (FIGS. 11A and 11B, respectively). FIGS. 11A-B show the effect of compound 1 on the production of A) intracellular IFNγ and B) IL-17 by $T_H$ cells induced by allogeneic activated DC in an MLR ("Ctrl" refers to T cells that did not have DCs added to them. *Denotes significance of P<0.05 using a two-tailed t test. Data points are shown±SEM).

The results suggest that compound 1 is not able to inhibit MHC II-Ii cleavage, as DCs treated with 10 µM 1 in the allogeneic (but not autologous) MLR were still able to stimulate T cell proliferation. Furthermore, compound 1 was able to downregulate pro-inflammatory cytokines in both types of assays. This indicates that either presentation of TTc is inhibited in both cases, with inhibition of cytokine production being a consequence of this, or that compound 1 has a direct effect on cytokine expression.

Example 15

Molecular Docking

Compounds 1 and 3 were docked into cathepsin D using the crystal structure of pepstatin A in cathepsin D as a starting point (PDB code 1LYB) (see Baldwin et al., *Proc. Natl. Acad. Sci. USA* 1993, 90, 6796-6800) AutoDock Vina 1.0 was used for all docking runs (Trott, O. et al., *J. Comput. Chem.* 2009, DOI: 10.1002/jcc.21334). This program is two orders of magnitude faster than AutoDock 4, and thus renders docking of flexible peptides with ~25-50 rotatable bonds possible on normal workstations in a reasonable timeframe.

The program was able to reproduce the docked conformation of pepstatin A in cathepsin D, with an RMSD of 0.977 Å. The default value of exhaustiveness (8) was sufficient to reproduce the bound conformation of pepstatin A, but since compounds 1 and 3 have more rotatable bonds, a higher value (25) was used for all docking studies, except where stated otherwise. In structures of grassystatins A (1) and C (3), all bonds were treated as rotatable, except ring and amide bonds, and the protein was treated as rigid.

For compound 1, the terminal amine was protonated to reflect its likely state at physiological pH. Apart from the Pro amide bond, all amides in the ligand were set to trans configuration. For each compound, separate structures were made with the Pro amide bond either cis or trans. Docking was carried out with an exhaustiveness value of 25, and a maximum output of 100 structures. It was observed that AutoDock was always able to propose docked structures with similar calculated affinities (~1-9 to −7 kcal/mol), and so the output structures were examined qualitatively. The primary criterion used in choosing the best docked structures was the position of the statine unit relative to the active site aspartates (Asp-33 and Asp-231), with reference to the bound conformation of pepstatin A. The rationale for this is found in the numerous crystal structures of pepstatin A and analogs bound to many different aspartic proteases (see, e.g., Bernstein et al., *J. Mol. Biol.* 2003, 329, 505-524; Borelli et al., *Proteins Struc. Func. Genet.* 2007, 68, 738-748; Fitzgerald et al., *J. Biol. Chem.* 1990, 265, 14209-14219; Fujimoto et al., *J. Mol. Biol.* 2004, 341, 1227-1235; Fujinaga et al., *Protein Sci.* 1995, 4, 960-972; Kamitori et al., *J. Mol. Biol.* 2003, 326, 1501-1511; Yang et al., *Acta Cryst. D* 1999, D55, 625-630; Asojo et al., *J. Mol. Biol.* 2003, 327, 173-181; Bone et al., *J. Am. Chem. Soc.* 1991, 113, 9382-9384; Coates et al., *Biochem.* 2001, 40, 13149-13157; Fraser et al., *Biochem.* 1992, 31, 5201-5214; and James et al., *Biochem.* 1992, 31, 3872-3886).

Docking to cathepsin E was carried out in the same manner, but with some differences. There is only one crystal structure of cathepsin E available (PDB code 1TZS) (Ostermann et al., *J. Mol. Biol.* 2004, 342, 889-899), where the inhibitory prodomain is still resident in the active site. This structure probably corresponds to an early intermediate in the maturation of the enzyme. In addition to the prodomain in the active site, the N-terminal region (Lys-14 to Asp-22) is blocking the active site tunnel so that the enzyme is in the closed conformation. A structure more consistent with the mature enzyme had to be produced in order to carry out effective docking. For this purpose, homology modeling was carried out using the SWISS-MODEL web server (see Arnold et al., *Bioinformatics* 2006, 22, 195-201). Amongst the protein structures in the PDB, human cathepsin E has the highest sequence homology with porcine pepsinogen (PDB code 2PSG) and its mature form, pepsin (PDB code 4PEP) (see Sielecki et al., *J. Mol. Biol.* 1991, 219, 671-692; and Sielecki et al., *J. Mol. Biol.* 1990, 214, 143-170).

The activation intermediate structure for cathepsin E (1TZS) agrees very well with that for pepsinogen (2PSG, RMSD 0.784 Å), therefore the structure of the corresponding mature enzyme (4PEP) is most likely a good template for homology modeling. The structure obtained was in excellent agreement with 1LYB (RMSD 0.833 Å). Docking of pepstatin A into the homology model was successful. The conformation obtained was close to that of pepstatin A bound to cathepsin D (RMSD 1.893 Å). Grassystatin A (1) was docked using the same protocol as above. For grassystatin C (3), a larger value of exhaustiveness was used (50).

To gain some insight into the structural basis for the selectivity of the grassystatins for cathepsin E over D, compounds 1 and 3 were docked into these two enzymes (FIG. 12). For both proteins, compounds 1 and 3 were successfully docked using AutoDock Vina 1.0, with the ligand treated as fully flexible (Trott et al., *J. Comput. Chem.* 2009, DOI: 10.1002/jcc.21334). To be consistent with the mode of cathepsin inhibition by pepstatin A, input structures of the ligands had all amide bonds trans, except the proline amide, for which separate cis and trans structures were produced. For cathepsin D, the crystal structure of pepstatin A bound to this enzyme was used for docking (PDB code 1LYB) (Baldwin et al., *Proc. Natl. Acad. Sci. USA* 1993, 90, 6796-6800). Pepstatin A was able to be successfully re-docked into this structure, prior to docking the ligands. For cathepsin E, homology modeling was used to obtain an appropriate starting structure, because the only crystal structure published is of an early activation intermediate (PDB code 1TZS) (*J. Mol. Biol.* 2004, 342, 889-899).

For the homology modeling, the structure of mature porcine pepsin (PDB code 4PEP), a protein with highly homologous primary sequence, was used as a template for the primary sequence of cathepsin E, taken from 1TZS (Sielecki et al., *J. Mol. Biol.* 1990, 214, 143-170). Pepstatin A was successfully docked into the resulting structure before docking of the compounds 1 and 3 was attempted.

Many of the putative hydrogen bond interactions suggested by the crystal structure of pepstatin A bound to cathepsin D (PDB code 1LYB) were also present in the model of compound 1 bound to this enzyme (FIG. 12A). The reduced affinity of compound 1 versus pepstatin A may be due to the presence of a polar residue at P2 (Val in pepstatin A and Asn in compound 1). Cathepsin D has an established preference for hydrophobic residues in this position, although it is somewhat tolerant of polar residues here (Rao-Naik et al., *Proteins Struc. Func. Genet.* 1995, 22, 168-181).

FIGS. 12 A-D show docked structures of grassystatins A (1) and C (3) with cathepsins D and E. For each the protein is shown, possible hydrogen bonds are shown as dotted lines. FIG. 12A shows docked conformation of grassystatin A (1) with cathepsin D. FIG. 12B shows the docked conformation of grassystatin A (1) with cathepsin E. FIG. 12C shows the docked conformation of grassystatin C (3) with cathepsin D. And FIG. 12D shows the docked conformation of grassystatin C (3) with cathepsin E.

In the docked conformation of compound 1, the Asn side chain is curled down in order to interact with Ser-80 in the flap, and to avoid the hydrophobic residues Met-307 and Met-309. The docked structure of grassystatin A (1) in cathepsin E (FIG. 12B) shows this unit interacting with the polar residue Gln-303, which replaces Met-307 in cathepsin D. This could be one reason for an increased affinity for cathepsin E versus D. Another factor could be the numerous hydrogen bond interactions possible between the O-Me-Pro unit of compound 1 with Gln-85 in cathepsin E (FIG. 12B). It is probably not possible to form so many hydrogen bonds with the equivalent residue in cathepsin D-His-77.

It was found that grassystatin C (3) was less potent than grassystatins A and B (1 and 2, respectively) against both cathepsins D and E. It is suspected that it is due to the absence of the terminal N,N-Me$_2$-Val, which could act as either a hydrogen bond donor (if protonated) or acceptor (if unprotonated) (Ghoneim et al., *Bioorg. Med. Chem.* 2006, 14, 6640-6658). In cathepsin D, there are several polar residues within reach of this unit (Tyr-10, Gln-14, Thr-125, Lys-130, Gln-258 and Gln-260). The situation is similar with cathepsin E, where there is a number of polar residues in the same pocket (Tyr-20, Glu-24, Glu-27, Glu-121, Asp-125, Glu-256 and Tyr-257). In the docked structure of compound 1 shown in FIG. 12B, the basic nitrogen of N,N-Me$_2$-Val is close to Gln-121. In the same run, another similar structure was produced, where the basic nitrogen was close to Tyr-20 (not shown). Thus, this unit may serve to anchor the inhibitor in the correct position within the binding cleft.

It was observed that when docking into the same protein structure, more spurious structures were produced for grassystatin C (3) than for grassystatin A (1) (for example, conformations where the N—C direction was reversed, where the ligand folded back on itself, or where a unit other than statine resided at the catalytic center). In these situations, because compound 3 has fewer rotatable bonds than compound 1, it is unlikely that the search parameters would be insufficient for compound 3 and not compound 1.

It was found that the central statine unit in pepstatin A is the pharmacophore of inhibition that binds to cathepsin D at the P1-P1' site (see FIG. 4 for sites) (Baldwin et al., *Proc. Natl. Acad. Sci. USA* 1993, 90, 6796-6800). If the binding mode is the same for compounds 1-3, then the units flanking the statine unit confer the differential activity for cathepsin D and E. It is suspected that cathepsin D strongly favors hydrophobic amino acids in the P2 position, compared to polar units such as Asn in compounds 1 and 2, or N-Me-Gln in compound 3, which are more tolerated by cathepsin E (see Scarborough et al., *Protein Eng.* 1994, 7, 495-502; and Rao-Naik et al., *Proteins Struc. Func. Genet.* 1995, 22, 168-181). This could explain why these compounds are less potent inhibitors against cathepsin D compared to pepstatin A, which has valine at P2 (see FIG. 4).

Both cathepsins D and E allow polar (but not charged) units at position P2', and hydrophobic units such as leucine are also allowed (see Rao-Naik et al., *Proteins Struc. Func. Genet.* 1995, 22, 168-181; and Arnold et al., *Eur. J. Biochem.* 1997, 249, 171-179). It was suspected the change from Thr in compounds 1 and 2 to Ile in compound 3 may not account for its lower activity. The putative hydrogen bond between Asn-NH and Ser-80-OH may be particularly important to binding and this interaction is not possible in 3 because the α-nitrogen of Gln is methylated. Compound 3 does not possess terminal units N,N-Me$_2$-L-Val-L-Hiva. The basic nitrogen of N,N-Me$_2$-Val is probably able to interact with acidic residues in both cathepsins D and E. As previously been shown that occupation of the S5 subsite of cathepsin E with Lys increases substrate turnover (Rao-Naik et al., *Proteins Struc. Func. Genet.* 1995, 22, 168-181), occupation of this site by positively charged residues may therefore be key to inhibitor binding.

While this invention has been particularly illustrated and described with reference to particular examples, it will be understood by those skilled in the art that various changes in form and details may be made therein without departing from the scope and spirit of the invention encompassed by the appended claims.

INCORPORATION BY REFERENCE

The contents of all references (including literature references, issued patents, published patent application, and co-pending patent applications) listed herein and/or cited throughout this application are hereby expressly incorporated in their entireties by reference.

What is claimed is:

1. An isolated compound selected from the group of grassystatins A, B and C as follows:

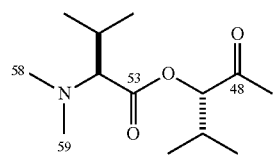

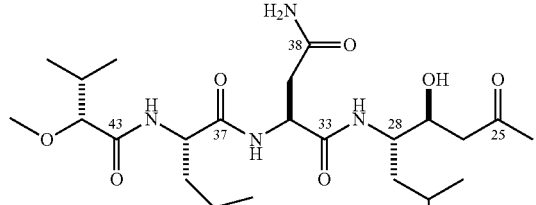

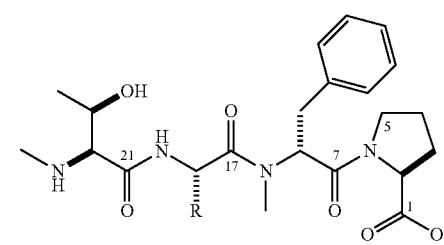

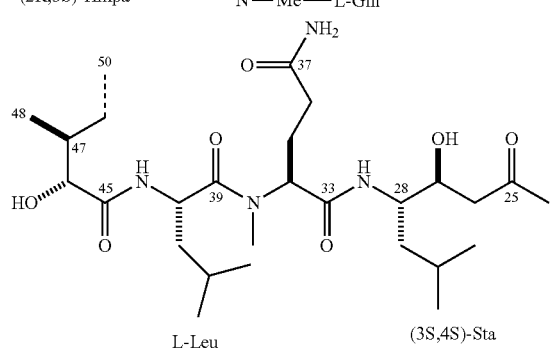

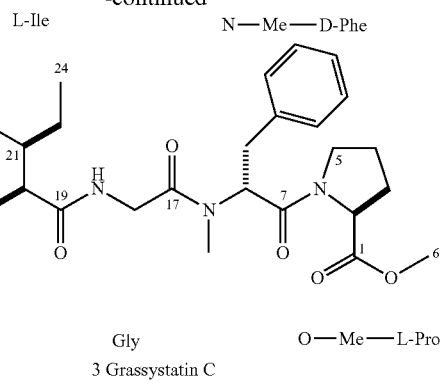

3 Grassystatin C or a pharmaceutically acceptable salt, ester, amide, hydrate, stereoisomer, or solvate thereof.

2. A pharmaceutical composition comprising a compound selected from the group of grassystatins A, B and C, or a pharmaceutically acceptable salt, ester, amide, hydrate, stereoisomer, or solvate thereof, together with a pharmaceutically acceptable carrier or diluent.

3. A method of treating a disease or disorder in a subject, the method comprising administering to the subject an effective amount of a compound selected from the group of grassystatins A, B and C, or a pharmaceutically acceptable salt, ester, hydrate, or solvate thereof, wherein the disease or disorder is selected from the group consisting of disorders of the cell cycle, neurodegenerative disorders, cancer, and Alzheimer's disease.

4. A method of inhibiting T-cell proliferation in a subject, the method comprising administering to the subject an effective amount of a compound selected from the group of grassystatins A and B, or a pharmaceutically acceptable salt, ester, hydrate, or solvate thereof.

5. The method of claim 4, comprising reducing IL-17 production in a subject or in a cell, the method comprising administering to the subject or the cell an effective amount of a compound selected from the group of grassystatins A and B, or a pharmaceutically acceptable salt, ester, hydrate, or solvate thereof.

6. The method of claim 4, comprising reducing IFN-γ production in a subject or in a cell, the method comprising administering to the subject or the cell an effective amount of a compound selected from the group of grassystatins A and B, or a pharmaceutically acceptable salt, ester, hydrate, or solvate thereof.

7. A method of treating a disease or disorder in a subject, the method comprising administering to the subject an effective amount of a compound selected from the group of grassystatins A and B, or a pharmaceutically acceptable salt, ester, hydrate, or solvate thereof, wherein the disease or disorder is selected from the group consisting of infection, autoimmune disorders, allergic diseases, and transplant rejection.

* * * * *

UNITED STATES PATENT AND TRADEMARK OFFICE
CERTIFICATE OF CORRECTION

PATENT NO. : 8,569,245 B2  
APPLICATION NO. : 13/380775  
DATED : October 29, 2013  
INVENTOR(S) : Hendrik Luesch Page 1 of 1

It is certified that error appears in the above-identified patent and that said Letters Patent is hereby corrected as shown below:

In the Specification

Column 1, Lines 18-20 should read:
STATEMENT OF RIGHTS TO INVENTIONS MADE UNDER FEDERALLY SPONSORED RESEARCH
This invention was made with Government support under Grant No. GM086210 awarded by the National Institutes of Health. The Government has certain rights in the invention.

Signed and Sealed this
Eighteenth Day of April, 2017

Michelle K. Lee
*Director of the United States Patent and Trademark Office*